(12) United States Patent
Kulmala et al.

(10) Patent No.: US 11,162,044 B2
(45) Date of Patent: Nov. 2, 2021

(54) RENEWABLE BASE OIL IN LUBRICANT FORMULATIONS

(71) Applicant: Neste Oyj, Espoo (FI)

(72) Inventors: Kari Kulmala, Porvoo (FI); Chris Castanien, Porvoo (FI); Fredrik Nissfolk, Porvoo (FI); Mika Kettunen, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/623,257

(22) PCT Filed: Jun. 15, 2018

(86) PCT No.: PCT/EP2018/065976
§ 371 (c)(1),
(2) Date: Dec. 16, 2019

(87) PCT Pub. No.: WO2018/234188
PCT Pub. Date: Dec. 27, 2018

(65) Prior Publication Data
US 2020/0181527 A1 Jun. 11, 2020

(30) Foreign Application Priority Data

Jun. 19, 2017 (FI) .................................. 20175569
Aug. 31, 2017 (FI) .................................. 20175780
(Continued)

(51) Int. Cl.
*C10M 105/00* (2006.01)
*C10M 105/04* (2006.01)
(Continued)

(52) U.S. Cl.
CPC ........... *C10M 105/04* (2013.01); *B01D 3/143* (2013.01); *B01J 21/04* (2013.01); *B01J 21/063* (2013.01);
(Continued)

(58) Field of Classification Search
CPC .............. C10G 3/50; C10G 2300/1003; C10G 2300/202; C10G 2300/1014;
(Continued)

(56) References Cited

U.S. PATENT DOCUMENTS 8,679,805 B2  3/2014  Chung et al.
9,523,061 B2  12/2016 Nelson et al.
(Continued)

FOREIGN PATENT DOCUMENTS

CN    1867653 A    11/2006
CN    102300967 A  12/2011
(Continued)

OTHER PUBLICATIONS

Eisner, et al., "The synthesis of long-chain, branched, hydroxyaliphatic compounds", Bull. Soc. Chim., 1995, pp. 212-218.
(Continued)

*Primary Examiner* — Taiwo Oladapo
(74) *Attorney, Agent, or Firm* — Buchanan Ingersoll & Rooney PC

(57) ABSTRACT

A $C_{31}$ renewable base oil is disclosed that is suitable as a base oil to provide low viscosity base oils, such as having both low Noack volatility and low CCS-30° C. viscosity and/or to provide low viscosity base oils at the same time having a combination of acceptable HTHS and KV100 to allow the industry's base oil blenders to formulate high quality engine oils, such as SAE grade 0W-20, 0W-16, 0W-12 or 0W-8.

31 Claims, 6 Drawing Sheets

(30) Foreign Application Priority Data

| Aug. 31, 2017 | (FI) | 20175781 |
| Aug. 31, 2017 | (FI) | 20175782 |
| Dec. 7, 2017 | (FI) | 20176095 |

(51) Int. Cl.

| B01J 21/04 | (2006.01) |
| B01J 21/06 | (2006.01) |
| B01J 23/883 | (2006.01) |
| B01J 35/10 | (2006.01) |
| C07C 45/41 | (2006.01) |
| C10G 3/00 | (2006.01) |
| C10G 45/58 | (2006.01) |
| C10L 1/08 | (2006.01) |
| B01J 29/85 | (2006.01) |
| C10G 67/02 | (2006.01) |
| C11C 1/04 | (2006.01) |
| C10M 105/06 | (2006.01) |
| C10M 169/04 | (2006.01) |
| B01D 3/14 | (2006.01) |
| C07C 51/44 | (2006.01) |
| C10M 177/00 | (2006.01) |
| C11C 1/10 | (2006.01) |
| C10N 30/00 | (2006.01) |
| C10N 20/00 | (2006.01) |
| C10N 30/02 | (2006.01) |
| C10N 30/04 | (2006.01) |
| C10N 30/10 | (2006.01) |
| C10N 30/12 | (2006.01) |
| C10N 30/14 | (2006.01) |
| C10N 30/16 | (2006.01) |
| C10N 70/00 | (2006.01) |

(52) U.S. Cl.
CPC ............ *B01J 23/883* (2013.01); *B01J 29/85* (2013.01); *B01J 35/1014* (2013.01); *B01J 35/1019* (2013.01); *B01J 35/1038* (2013.01); *B01J 35/1061* (2013.01); *C07C 45/41* (2013.01); *C07C 51/44* (2013.01); *C10G 3/46* (2013.01); *C10G 3/49* (2013.01); *C10G 3/50* (2013.01); *C10G 45/58* (2013.01); *C10G 67/02* (2013.01); *C10L 1/08* (2013.01); *C10M 105/06* (2013.01); *C10M 169/04* (2013.01); *C10M 177/00* (2013.01); *C11C 1/04* (2013.01); *C11C 1/10* (2013.01); *C10G 3/44* (2013.01); *C10G 2300/1003* (2013.01); *C10G 2300/1014* (2013.01); *C10G 2300/1018* (2013.01); *C10G 2300/202* (2013.01); *C10G 2300/301* (2013.01); *C10G 2300/302* (2013.01); *C10G 2300/304* (2013.01); *C10G 2300/308* (2013.01); *C10G 2300/4006* (2013.01); *C10G 2300/4012* (2013.01); *C10G 2300/4018* (2013.01); *C10G 2400/04* (2013.01); *C10G 2400/10* (2013.01); *C10L 2200/0484* (2013.01); *C10L 2270/026* (2013.01); *C10L 2290/543* (2013.01); *C10M 2203/022* (2013.01); *C10M 2203/0206* (2013.01); *C10M 2203/045* (2013.01); *C10M 2203/065* (2013.01); *C10N 2020/065* (2020.05); *C10N 2020/067* (2020.05); *C10N 2030/02* (2013.01); *C10N 2030/04* (2013.01); *C10N 2030/10* (2013.01); *C10N 2030/12* (2013.01); *C10N 2030/14* (2013.01); *C10N 2030/16* (2013.01); *C10N 2030/43* (2020.05); *C10N 2030/74* (2020.05); *C10N 2070/00* (2013.01)

(58) Field of Classification Search
CPC .... C10G 2300/4006; C10G 2300/4012; C10G 2300/4018; C10G 2400/04; C10G 2400/10; C10G 67/02; C10G 3/46; C10G 3/49; C10G 45/58; B01J 29/85; B01J 21/04; B01J 21/063; B01J 23/883; B01J 35/1014; B01J 35/1019; B01J 35/1038; B01J 35/1061; C11C 1/04; C07C 45/41; C10N 2030/74; C10N 2020/067; C10N 2020/065; C10N 2030/02; C10N 2030/04; C10N 2030/10; C10N 2030/12; C10N 2030/14; C10N 2030/16; C10N 2020/02; C10N 2020/071; C10N 2020/085; C10N 2030/08; C10N 2070/00; C10M 2203/0206; C10M 2203/022; C10M 2203/045; C10M 2203/065; C10M 105/04; C10M 105/06; C10M 169/04; C10L 2290/543; C10L 2200/0484; C10L 2270/026; C10L 1/08; Y02E 50/10; Y02P 30/20

See application file for complete search history.

(56) References Cited

U.S. PATENT DOCUMENTS

| 2005/0077208 | A1 | 4/2005 | Miller et al. |
| 2005/0263435 | A1 | 12/2005 | Skledar et al. |
| 2007/0135663 | A1 | 6/2007 | Aalto et al. |
| 2007/0161832 | A1 | 7/2007 | Myllyoja et al. |
| 2007/0244018 | A1 | 10/2007 | Visger et al. |
| 2008/0034645 | A1 | 2/2008 | Bressler |
| 2009/0014354 | A1 | 1/2009 | Knuuttila et al. |
| 2010/0234654 | A1 | 9/2010 | Wang et al. |
| 2011/0107656 | A1 | 5/2011 | Miller |
| 2012/0220506 | A1 | 8/2012 | Qin et al. |
| 2013/0190544 | A1 | 7/2013 | Wang et al. |
| 2013/0217606 | A1* | 8/2013 | Wang ................. C10M 169/041 508/449 |
| 2014/0046104 | A1 | 2/2014 | Mcneff et al. |
| 2014/0115955 | A1 | 5/2014 | Mcneff et al. |
| 2014/0171703 | A1 | 6/2014 | Wang et al. |
| 2014/0323665 | A1 | 10/2014 | Wu et al. |
| 2014/0335586 | A1 | 11/2014 | Zhang et al. |
| 2015/0018581 | A1 | 1/2015 | Kettunen et al. |
| 2015/0018588 | A1 | 1/2015 | Myllyoja et al. |
| 2015/0183915 | A1 | 7/2015 | Johnson et al. |
| 2015/0251168 | A1 | 9/2015 | Kettunen et al. |
| 2016/0137944 | A1 | 5/2016 | Liang et al. |
| 2017/0088789 | A1 | 3/2017 | Grisso et al. |
| 2017/0240832 | A1* | 8/2017 | Hahn ................... C10M 101/02 |
| 2017/0334806 | A1 | 11/2017 | Agee |
| 2017/0362154 | A1* | 12/2017 | Kettunen ................ B01J 23/04 |
| 2018/0171252 | A1 | 6/2018 | Fourage et al. |
| 2020/0181503 | A1 | 6/2020 | Myllyoja et al. |
| 2020/0181504 | A1 | 6/2020 | Myllyoja et al. |
| 2021/0139786 | A1 | 5/2021 | Toppinen et al. |
| 2021/0139787 | A1 | 5/2021 | Myllyoja et al. |

FOREIGN PATENT DOCUMENTS

| CN | 102906229 A | 1/2013 |
| CN | 103773442 A | 5/2014 |
| DE | 102009017827 A1 | 10/2010 |
| DK | 2809745 A1 | 12/2014 |
| EP | 1741767 A1 | 1/2007 |
| EP | 1741768 A1 | 1/2007 |
| EP | 1741767 B1 | 7/2015 |
| EP | 2809745 B1 | 4/2016 |
| EP | 3012310 A1 | 4/2016 |

(56) References Cited

FOREIGN PATENT DOCUMENTS

| | | | |
|---|---|---|---|
| JP | 2004124080 A | 4/2004 | |
| WO | 00/68799 A1 | 11/2000 | |
| WO | 2007061698 A2 | 5/2007 | |
| WO | 2007068795 A1 | 6/2007 | |
| WO | 2007068800 A2 | 6/2007 | |
| WO | 2008152200 A1 | 12/2008 | |
| WO | 2012156679 A1 | 11/2012 | |
| WO | 2013113976 A1 | 8/2013 | |
| WO | 2014099371 A2 | 6/2014 | |
| WO | 2014099373 A1 | 6/2014 | |
| WO | 2016061050 A1 | 4/2016 | |
| WO | 2016062868 A1 | 4/2016 | |
| WO | WO-2016061050 A1 * | 4/2016 | .......... C10M 105/04 |
| WO | WO-2016062868 A1 * | 4/2016 | .............. C10G 3/42 |
| WO | 2017001606 A1 | 1/2017 | |

OTHER PUBLICATIONS

International Search Report (PCT/ISA/210) and Written Opinion (PCT/ISA/237) dated Aug. 17, 2018, by the European Patent Office as the International Searching Authority for International Application No. PCT/EP2018/065976.
Rush, et al., "Generation of unusual branched long chain alkanes from hydrous pyrolysis of anamox bacterial biomass", Organic Geochemistry, 2014, vol. 76, pp. 136-145.
Tamai, et al., "Estimation of flow activation vol. of synthetic ester lubricants", J. Japan Petrol. Inst., 1982, vol. 25, No. 5, pp. 281-285.
Toubiana, et al., "Long-chain aliphatic substances related to bacterial lipids", Ann. Chim., 1962, vol. 7, pp. 593-642.
Deffense Etienne, "From Organic Chemistry to Fat and Oil Chemistry", OCL, vol. 16, No. 1, 2009, pp. 14-24.
International Preliminary Report on Patentability received for PCT Application No. PCT/EP2018/065971, dated Jan. 2, 2020, 8 pages.
International Search Report (PCT/ISA/210) and Written Opinion (PCT/ISA/237) received for PCT Application No. PCT/EP2018/065971, dated Jul. 19, 2018, 10 pages.
International Preliminary Report on Patentability received for PCT Application No. PCT/EP2018/065973, dated Jan. 2, 2020, 7 pages.
International Search Report and Written Opinion received for PCT Application No. PCT/EP2018/065973, dated Jul. 19, 2018, 9 pages.
International Search Report (PCT/ISA/210) and Written Opinion (PCT/ISA/237) received for PCT Application No. PCT/EP2018/065978, dated Sep. 13, 2018, 16 pages.
International Search Report (PCT/ISA/210) and Written Opinion (PCT/ISA/237) received for PCT Application No. PCT/EP2018/065980, dated Jul. 25, 2018, 10 pages.
Non Final Office Action dated Mar. 31, 2021, by the U.S. Patent and Trademark Office in U.S. Appl. No. 16/623,188, 10 pages.
Restriction Requirement dated Jan. 28, 2021, by the U.S. Patent and Trademark Office in U.S. Appl. No. 16/623,276, 7 pages.
Non Final Office Action dated Jan. 6, 2021, by the U.S. Patent and Trademark Office in U.S. Appl. No. 16/623,306, 16 pages.
Notice of Allowance dated Jul. 6, 2021, by the U.S. Patent and Trademark Office in U.S. Appl. No. 16/623,306.
Notice of Allowance dated Jun. 18, 2021, by the U.S. Patent and Trademark Office in U.S. Appl. No. 16/623,210.
Notice of Allowance dated Jul. 12, 2021, by the U.S. Patent and Trademark Office in U.S. Appl. No. 16/623,188.
Office Action dated Jul. 2, 2021, by the U.S. Patent and Trademark Office in U.S. Appl. No. 16/623,276.
First Office Action dated Jul. 2, 2021, by the Chinese Patent Office in corresponding Chinese Patent Application No. 201880039835.4, and an English Translation of the Office Action. (7 pages).

* cited by examiner

Figure 1 – GC Chromatograms of HDO and isomerisation products
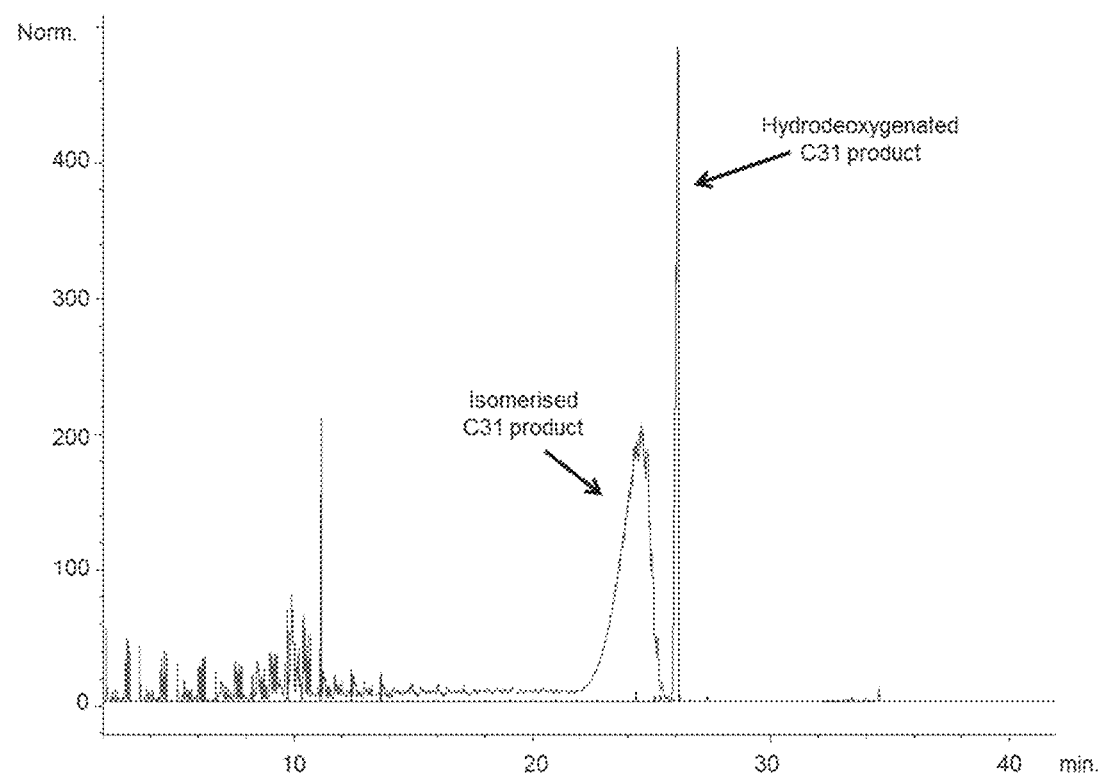

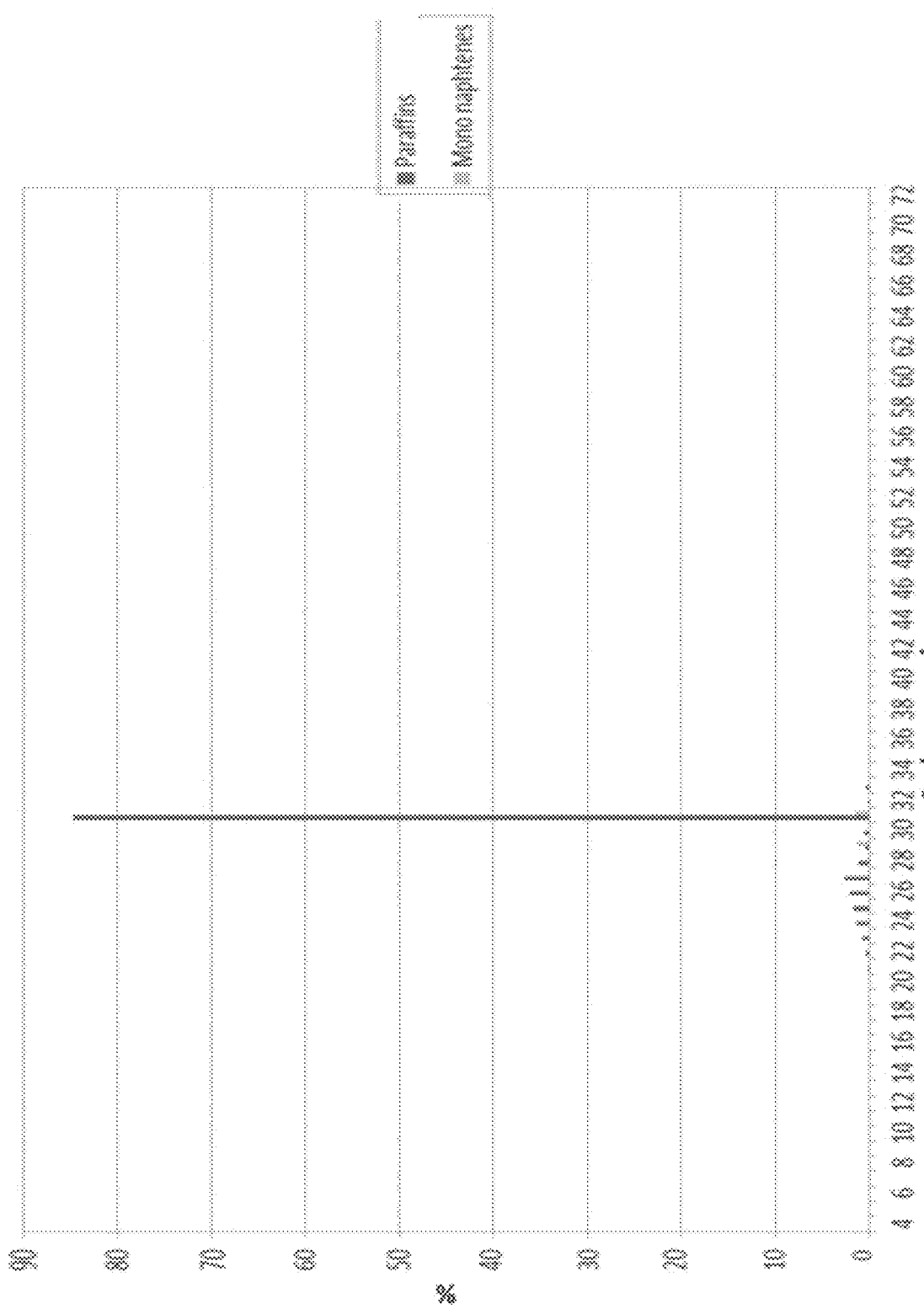
Figure 2 – FIMS analysis of $C_{31}$ base oil, Table 1 (f)

Figure 3 – FIMS analysis of paraffins in $C_{31}$ base oil, table 1 (A-K)
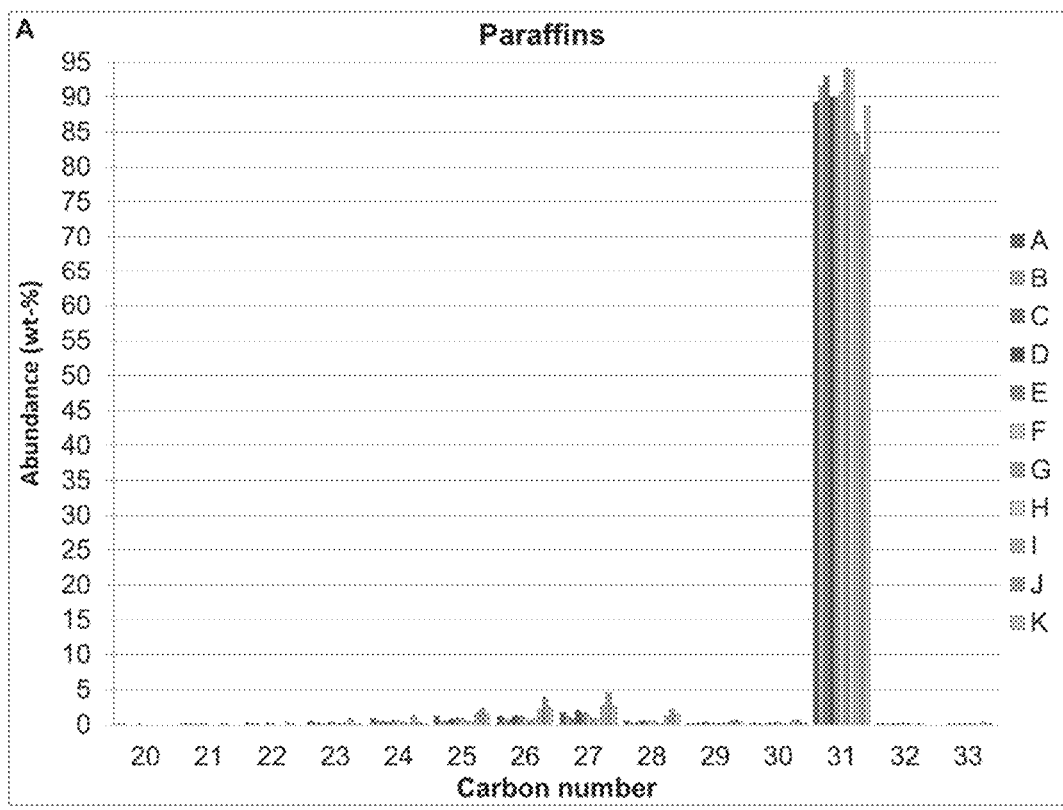
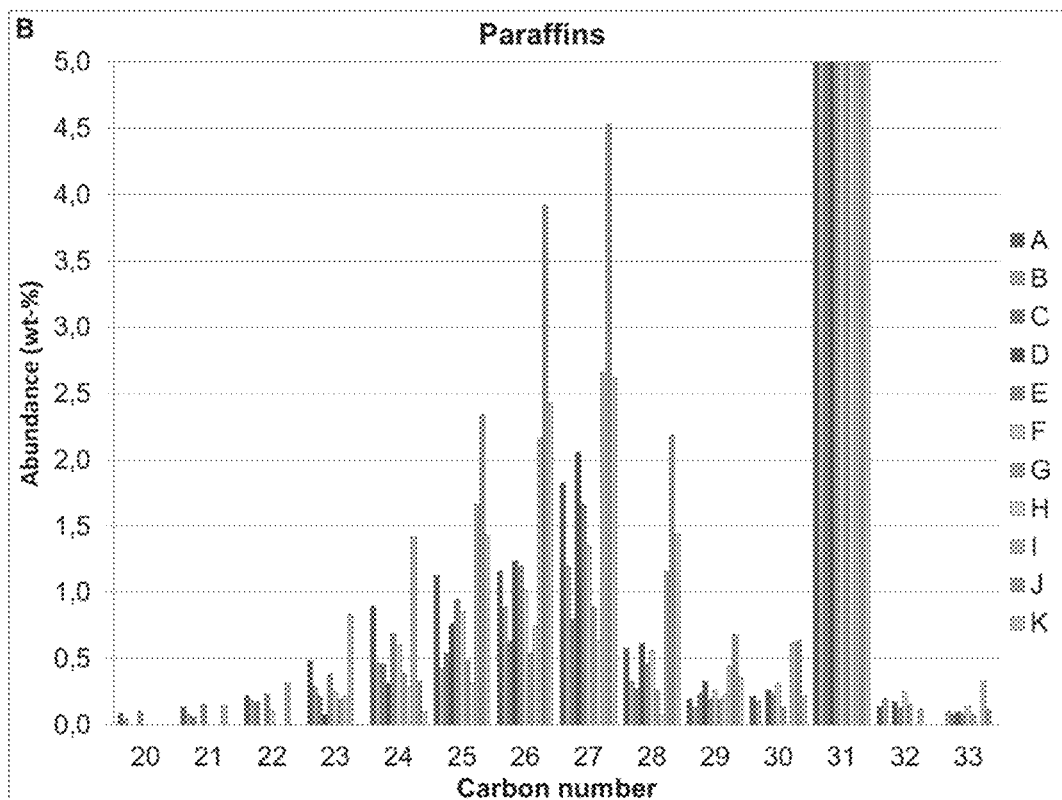

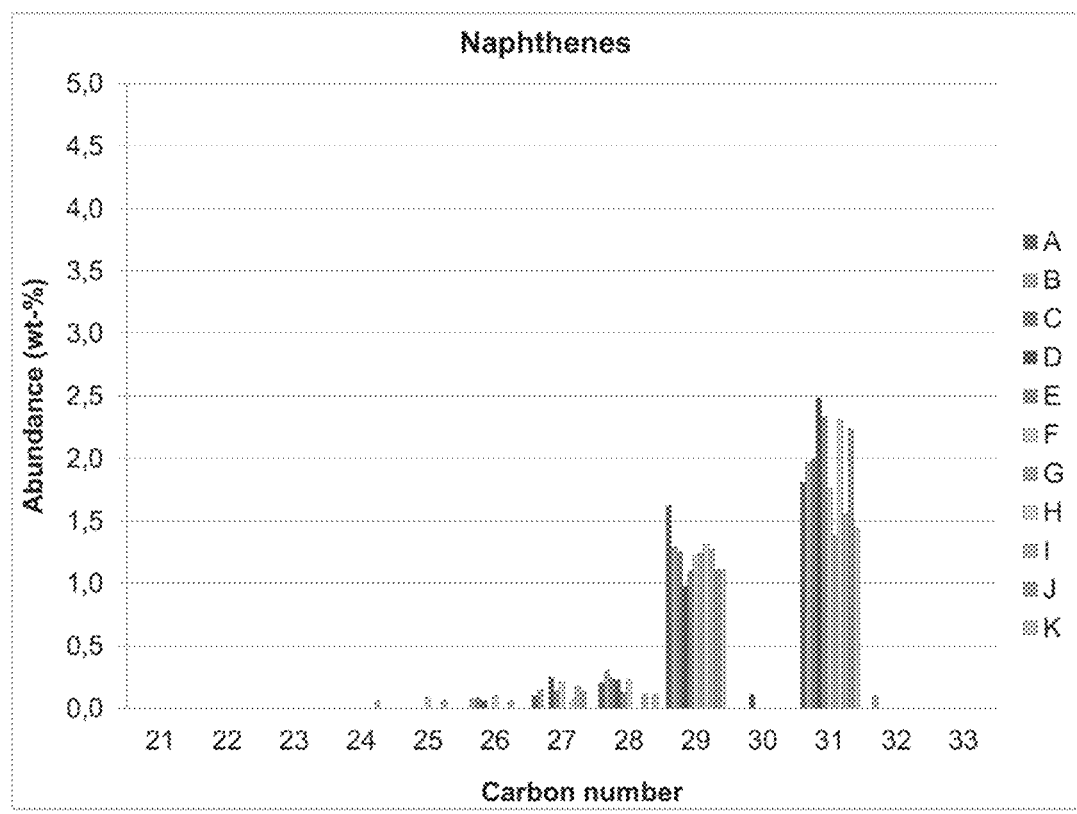
Figure 4 – FIMS analysis of naphthenes in $C_{31}$ base oil, table 2 (A-K)

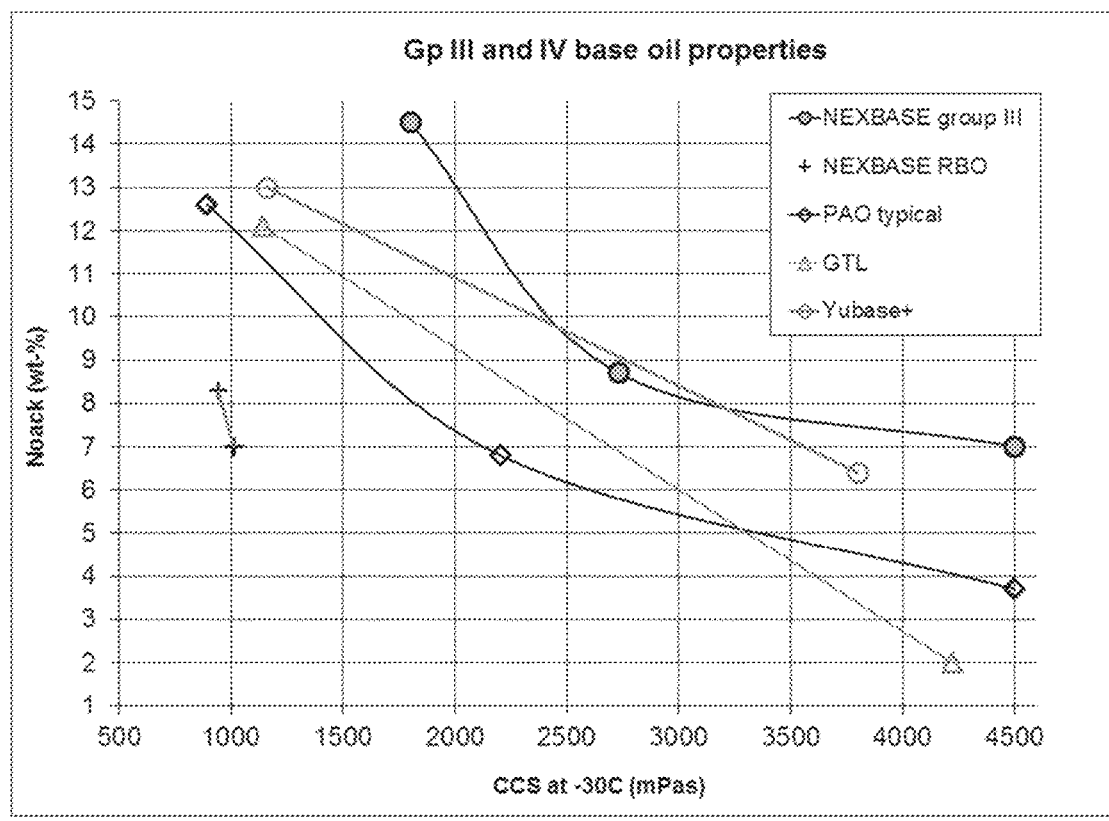
Figure 5 – Noack – CCS combined performance of low viscosity base oils

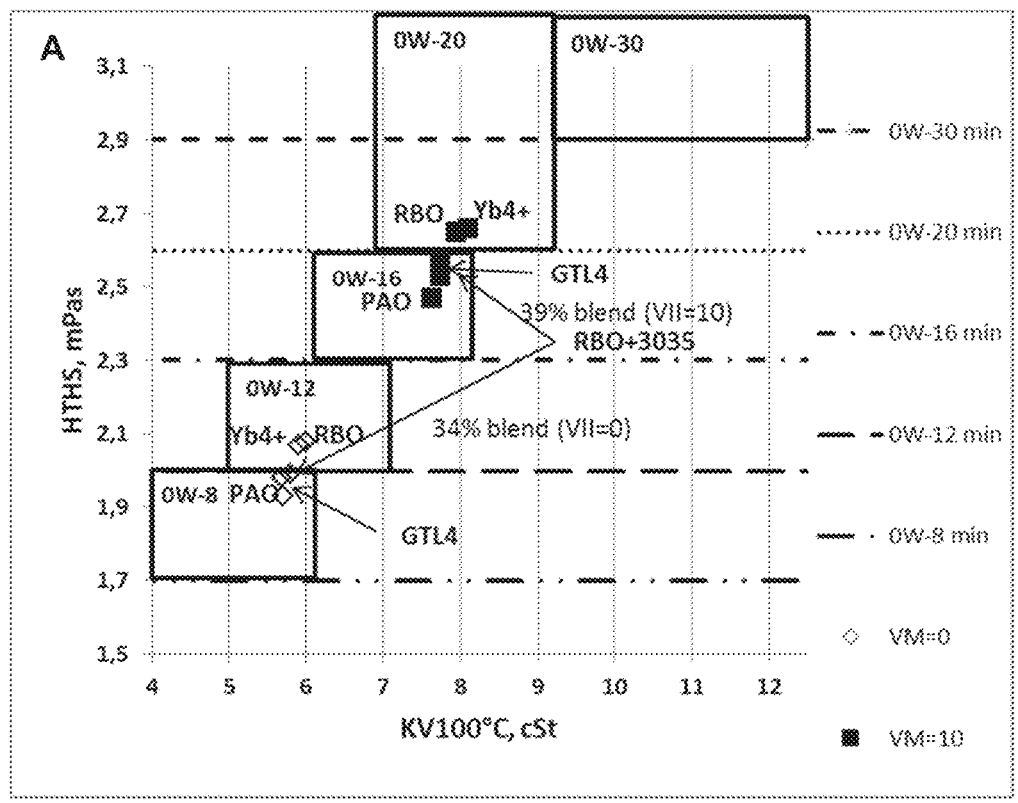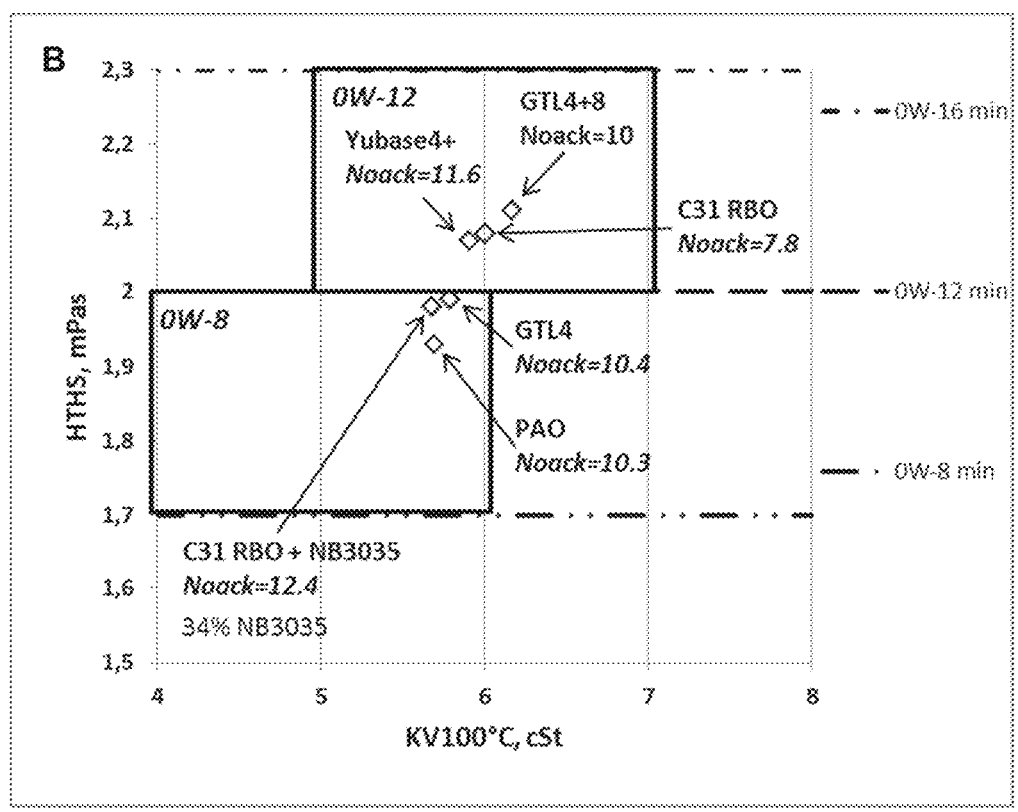
Figure 6 – SAE Grades (J300) and blends of $C_{31}$ base oil

RENEWABLE BASE OIL IN LUBRICANT FORMULATIONS

RELATED APPLICATION

This application is a national stage entry of PCT/EP2018/065976, filed Jun. 15, 2018, which claims priority to Finnish Patent Application No. 20176095, filed Dec. 7, 2017, which claims priority to Finnish Patent Application No. 20175782, filed Aug. 31, 2017, which claims priority to Finnish Patent Application No. 20175781, filed Aug. 31, 2017, which claims priority to Finnish Patent Application No. 20175780, filed Aug. 31, 2017, which claims priority to Finnish Patent Application No. 20175569, filed Jun. 19, 2017, which are incorporated by reference in their entirety.

TECHNICAL FIELD

The present invention relates to the field of lubricating oils, in particular to lubricating oil compositions comprising novel renewable base oil (RBO) compositions displaying superior lubrication properties, as well as base oil mixtures comprising novel renewable base oil (RBO) compositions and novel a $C_{31}$ renewable base oil composition. The $C_{31}$ renewable base oil composition, a base oil mixture comprising the RBO, and lubricating oil compositions comprising such base oil mixtures are useful for reducing Noack volatility and/or kinematic viscosity of lubricating compositions, in particular lubricating compositions for internal combustion engines, such as passenger car motor oils.

BACKGROUND ART

Fluid film lubrication is important in order to reduce friction between surfaces in proximity and moving relative to each other. Without lubrication or with insufficient lubrication such friction will lead to increased heat and wear.

Base oils are used to manufacture products including lubricants, motor oil and metal processing fluids. Some of the important factors in the base oil are the viscosity at various temperatures which are important for the lubrication; the Noack volatility, which is important to reduce evaporation of the oil thereby increasing the oil change service intervals of e.g. passenger cars. In particular the performance of a lubricating oil in a passenger car to the cold-cranking simulator viscosity is important. The cold-cranking simulator was designed as a method of determining the low temperature performance of lubricants, in the specific condition of "cold cranking"—i.e. starting a cold engine.

It is desirably that passenger car motor oils have low Noack volatility to increase oil change service intervals of the car, as well as low cold cranking simulator viscosity (e.g. measured at −30° C., often abbreviated CCS-30° C.). However, there is typically a trade-off between these two properties, in that a low Noack volatility typically results in a high CCS-30° C. viscosity, and conversely that a low CCS-30° C. viscosity typically results in a high Noack volatility.

Another property, the high temperature high shear (HTHS) viscosity is an important property, which relates to the fuel economy and durability of a running engine. The High Temperature High Shear (HTHS) and kinematic viscosity at 100° C. (KV100) are two of the important properties of low viscosity SAE grade oils.

Only a few types of base oils having a combination of low Noack volatility and low CCS-30° C. viscosity exist and/or the combination of acceptable HTHS and KV100 that allow the industry's base oil blenders to formulate high quality engine oils, such as SAE grade 0W-20, 0W-16, 0W-12 or 0W-8.

Poly-alphaolefin oligomers of 1-decene (PAO) can be manufactured to have a low viscosity and low Noack volatility, which are needed for formulation of SAE grade 0W-XX lube oils. However, PAO base oils are expensive compared to other base oils and further are based on the availability of the 1-decene raw material, which currently have limited availability.

WO 2007/068795 A1 (to Neste Oil Oyj) relates to a process for producing hydrocarbon base oil from different feedstocks comprising $C_1$-$C_{38}$ carboxylic acids, including unsaturated carboxylic acids, preferably of biological origin, and the examples involve ketonisation in the gas phase, hydrodeoxygenation, and isomerization steps. The base oils produced in WO 2007/068795 A1 contain in addition to branched hydrocarbons preferably 5-20 wt % mono-naphthenes and less than 1 wt % of polycyclic naphthenes, and while the Noack volatility in one example is low compared to PAO base oils, the CCS-30° C. viscosity is higher, which might be due to the trade-off between these two properties. HTHS were not disclosed, and no specific SAE grade engine oils were disclosed.

Consequently, there is a need for lubricating compositions, in particular engine oils, which suffer less from the trade-off between Noack volatility and CCS-30° C. viscosity that is seen from existing low-viscosity oils. Additionally, there is a need for base oils which enable and provide flexibility to the industry's base oil blenders to formulate high quality engine oils, such as SAE grade 0W-20, 0W-16, 0W-12 or 0W-8.

Additionally, there is a need for further low-viscosity base oil products, in particular products that are not constrained by limited olefin availability or potential future depletion of fossil resources.

SUMMARY OF THE INVENTION

The present invention was made in view of the prior art described above, and the object of the present invention is to provide low viscosity base oils, in particular having both low Noack volatility and low CCS-30° C. viscosity and/or to provide low viscosity base oils at the same time having combination of acceptable HTHS and KV100 to allow the industry's base oil blenders to formulate high quality engine oils, such as SAE grade 0W-20, 0W-16, 0W-12 or 0W-8.

To solve the problem, the present invention provides lubricating oil compositions, for example lubricating oil compositions for internal combustion engines comprising: a) a base oil mixture comprising at least 13 wt % of a renewable base oil; the remainder selected from one or more base oils in the same or different API (American Petroleum Institute) category; wherein the amounts of base oils given in wt % are based on the total base oil mixture; b) one or more performance additives; wherein the renewable base oil comprises: more than 60 wt % $C_{31}$ alkanes, preferably more than 80 wt % $C_{31}$ alkanes; wherein the amounts of renewable base oil is given in wt % based on the renewable base oil;

The weight percentages of the hydrocarbon composition of the renewable base oil may be measured using field ionisation mass spectrometry (FI-MS).

That is, the inventors of the present invention in a first aspect of the invention found that including the $C_{31}$ renewable base oil obtainable from the $C_{16}$ fatty acids present in palm oil and other renewable feedstocks has superior properties in relation to both low Noack volatility and low CCS-30° C. viscosity (FIG. 5) as well as having a combination of acceptable HTHS and KV100 to allow the industry's base oil blenders to formulate high quality engine oils, such as SAE grade 0W-20, 0W-16, 0W-12 or 0W-8 (FIG. 6).

Additionally, the renewable character of the fatty acid feedstock for the renewable base oil of the present invention provides for a stronger security of supply to the industry's base oil blenders compared to base oils that could be constrained by limited alpha-olefin availability or by a potential future depletion of fossil resources.

At least one or more of the performance additives of the lubricating oil composition may be selected from the list consisting of: antioxidants, metal deactivators, corrosion inhibitors, detergents, dispersants, antiwear additives, friction modifiers, pour point depressants, viscosity improvers, foam inhibitors, thickeners, demulsifiers, emulsifiers, bactericides, fungicides and tackiness additives.

The lubricating oil composition may be formulated to meet the specifications for 0W-XX, such as any one of 0W-20, 0W-16, 0W-12, or 0W-8. The $C_{31}$ renewable base oil allows formulation of very low-viscosity grades meeting the specifications for 0W-12, or meeting the specifications even for 0W-8.

The renewable base oil of the lubricating composition may further be defined as comprising one or more of the following features:
less than 20 wt % $C_{32}$ or higher alkanes, preferably less than 10 wt % $C_{32}$ or higher alkanes;
the alkanes comprising 70 wt % or more iso-alkanes;
less than 1 wt % of oxygen-containing compounds;
between 1 wt % and 20 wt % $C_{20}$-30 alkanes;
between 0.1 wt % and 20 wt % $C_{32}$ or higher alkanes preferably less than 10 wt % $C_{32}$ or higher alkanes, such as $C_{32}$-$C_{48}$ alkanes,
between 1 wt % and 8 wt % $C_{25}$-32 cycloalkanes;
less than 1 wt % aromatic hydrocarbons;
less than 2 wt % di-, tri-, tetra-naphthenes, or higher;
the combined amount of $C_{29}$ and $C_{30}$ alkanes in wt % is less than the combined amount of $C_{26}$ and $C_{27}$ alkanes in wt %;
the combined amount of $C_{29}$ and $C_{31}$ cycloalkanes in wt % being more than the combined amounts of $C_{25}$, $C_{26}$, $C_{27}$, $C_{28}$, $C_{30}$ cycloalkanes.

The weight percentages of the hydrocarbons may be measured using field ionisation mass spectrometry (FI-MS).

The renewable base oil of the lubricating composition may further be defined as comprising one or more of the following features:
less than 20 wt % $C_{32}$ or higher alkanes, preferably less than 10 wt % $C_{32}$ or higher alkanes;
the alkanes comprising 70 wt % or more iso-alkanes;
less than 1 wt % of oxygen-containing compounds;

The weight percentages of the hydrocarbons may be measured using field ionisation mass spectrometry (FI-MS).

The renewable base oil of the lubricating composition may further be defined as comprising one or more of the following features:
between 1 wt % and 20 wt % $C_{20}$-30 alkanes;
between 0.1 wt % and 20 wt % $C_{32}$ or higher alkanes preferably less than 10 wt % $C_{32}$ or higher alkanes, such as $C_{32}$-$C_{48}$ alkanes,
between 1 wt % and 8 wt % $C_{25}$-32 cycloalkanes;
less than 1 wt % aromatic hydrocarbons;
less than 2 wt % di-, tri-, tetra-naphthenes, or higher;

The weight percentages of the hydrocarbons may be measured using field ionisation mass spectrometry (FI-MS).

The renewable base oil of the lubricating composition may further be defined as comprising one or more of the following features:
the combined amount of $C_{29}$ and $C_{30}$ alkanes in wt % is less than the combined amount of $C_{26}$ and $C_{27}$ alkanes in wt %;
and/or
the combined amount of $C_{29}$ and $C_{31}$ cycloalkanes in wt % being more than the combined amounts of $C_{25}$, $C_{26}$, $C_{27}$, $C_{28}$, $C_{30}$ cycloalkanes;

The weight percentages of the hydrocarbons may be measured using field ionisation mass spectrometry (FI-MS).

The lubricating oil compositions may further be functionally characterised by having one or more of the following properties:
a boiling point of between 350° C. and 650° C. as measured using Simulated distillation AC750 using EN 15199-2;
a viscosity index (VI) of more than 140 as measured using ASTM D2270
a Noack volatility number of less than 10 wt % as measured using ASTM D5800 or CECL-40-93-B
a pour point of –6° C. or lower as measured using ASTM D7346;
a Cold-Cranking Simulator viscosity (CCS-35° C.) value of less than 1800 cP as measured using ASTM D5293;
a kinematic viscosity (KV100) of less than 5 cSt using EN ISO 3104.

The lubricating oil compositions may further be functionally characterised by the renewable base oil having at least the following properties:
a Noack volatility number of less than 10 wt % as measured using ASTM D5800 or CECL-40-93-B; and
a kinematic viscosity (kV100) of less than 5 cSt using EN ISO 3104.

The lubricating oil composition may be characterised in that the base oil has a kinematic viscosity at 100° C. of 16 cSt as measured using ASTM D445; and the composition has a Noack volatility of at most 11% as measured using CECL-40-93-B.

The lubricating oil composition may be characterised in that the renewable base oil is present in an amount of at least 35 wt % based on the total base oil mixture, such as at least 50 wt %, for example at least 60 wt % based on the total base oil mixture.

The base oil mixture of the lubricating oil composition may in addition to the at least 13 wt % of a renewable base oil, comprise two or more base oils in the same or different API category.

The lubricating oil composition may comprise 10-50 wt % based on the total base oil mixture of a Group II and/or Group III base oil.

The lubricating oil composition may be characterised in that the base oil mixture contains no more than 10 wt % of a polyalphaolefin base oil. For example the lubricating oil composition may be characterised in that the base oil mixture is essentially free of polyalphaolefin base oil, preferably wherein the base oil mixture is free of polyalphaolefin base oil.

The lubricating oil composition may be characterised in that the base oil mixture contains no more than 10 wt % of a Fischer-Tropsch derived base oil. For example the lubricating oil composition may be characterised in that the base oil mixture is essentially free of Fischer-Tropsch derived base oil, preferably wherein the base oil mixture is free of Fischer-Tropsch derived base oil.

The lubricating oil composition may have a content of the renewable base oil of between 15-100 wt %, such as between 15-95 wt %, for example between 20-90 wt % based on the total base oil mixture.

The present invention is based on the novel $C_{31}$ base oils having more than 60 wt % $C_{31}$ alkanes, which may form part of the lubricating oil compositions of the present invention as well as forming part of the base oil mixtures of the present invention to obtain low viscosity base oils, in particular having both low Noack volatility and low CCS-30° C. viscosity and/or to provide low viscosity base oils at the same time having combination of acceptable HTHS and KV100 to allow the industry's base oil blenders to formulate high quality engine oils, such as SAE grade 0W-20, 0W-16, 0W-12 or 0W-8.

The weight percentages of the hydrocarbons below may be measured using field ionisation mass spectrometry (FI-MS).

The base oil composition is preferably of renewable origin and may comprise:
  more than 60 wt % $C_{31}$ alkanes;
  less than 20 wt % $C_{32}$ or higher alkanes, preferably less than 10 wt % $C_{32}$ or higher alkanes;
  the alkanes comprising 70 wt % or more iso-alkanes;
  less than 9 wt %, preferably less than 4.5 wt % cycloalkanes. For example less than 8 wt % $C_{25}$-32 cycloalkanes;

The base oil composition may be further characterised in that it may comprise:
  between 1 wt % and 10 wt % $C_{20}$-30 alkanes;

The base oil composition may be further characterised in that:
  the combined amount of $C_{29}$ and $C_{30}$ alkanes in wt % being less than the combined amount of $C_{26}$ and $C_{27}$ alkanes in wt %;
  and/or
  the combined amount of $C_{29}$ and $C_{31}$ cycloalkanes in wt % being more than the combined amounts of $C_{25}$, $C_{26}$, $C_{27}$, $C_{28}$, $C_{30}$ cycloalkanes.

In particular the base oil composition is mainly paraffinic with few and low amounts of impurities. Accordingly, the renewable base oil composition may be further characterised in that it has:
  less than 0.5 wt % aromatic hydrocarbons;
  less than 0.5 wt % di-, tri-, tetra-naphthenes, or higher;
  less than 1 wt % of oxygen-containing compounds, preferably less than 0.5 wt %
  less than 300 ppm sulfur content as measured using ASTM D 3120;
  less than 100 ppm nitrogen content as measured using ASTM D 4629.

The base oil compositions may further be functionally characterised by having one or more of the following properties:
  a boiling point of between 350° C. and 650° C. as measured using ASTM D7500, for example 380-650° C., 400-620° C., 420-600° C. measured either as the range between the IBP and FBP points or between the 5% and 95% distillation points;
  a viscosity index (VI) of more than 140 as measured using ASTM D2270
  a Noack volatility number of less than 10 wt % as measured using ASTM D5800 or CECL-40-93-B;
  a pour point of less than −10° C. as measured using ASTM D7346;
  a Cold-Cranking Simulator viscosity (CCS-35° C.) value of less than 1800 mPas as measured using ASTM D5293;
  a Cold-Cranking Simulator viscosity (CCS-30° C.) value of less than 1300 mPas as measured using ASTM D5293;
  a kinematic viscosity (KV100) of less than 5 mm$^2$/s using EN ISO 3104.

For example the base oil compositions may be functionally characterised by having at least the following two properties:
  a Noack volatility number of less than 10 wt % as measured using ASTM D5800 or CECL-40-93-B; and
  a kinematic viscosity (KV100) of less than 5 mm$^2$/s using EN ISO 3104.

The $C_{31}$ base oil composition of the present invention may be part of a base oil mixture with other base oils. A base oil mixture, for example a base oil mixture for internal combustion engines comprising at least 13 wt % of the $C_{31}$ base oil as defined above; the remainder selected from one or more base oils in the same or in different API (American Petroleum Institute) category; wherein the amounts given in wt % are based on the total base oil mixture.

The $C_{31}$ base oil amount of the base oil mixture may be present in an amount of at least 35 wt % based on the total base oil mixture, such as in an amount of at least 50 wt % based on the total base oil mixture.

The base oil mixture may in addition to the at least 13 wt % of a renewable base oil, comprise two or more base oils in the same or different API category.

The base oil mixture may comprise 10-50 wt % based on the total base oil mixture of a Group II and/or Group III base oil.

The base oil mixture may contain no more than 10 wt % of an polyalphaolefin base oil. For example, the base oil mixture may be essentially free of polyalphaolefin base oil, preferably wherein the base oil mixture is free of polyalphaolefin base oil.

The base oil mixture may contain no more than 10 wt % of a Fischer-Tropsch derived base oil. For example, the base oil mixture may be essentially free of Fischer-Tropsch derived base oil, preferably wherein the base oil mixture is free of Fischer-Tropsch derived base oil.

The base oil mixture may have a content of the $C_{31}$ base oil of the present invention of between 15-100 wt %, such as between 15-95 wt %, for example between 20-90 wt % based on the total base oil mixture.

The $C_{31}$ base oil according to the present invention can be used for reducing the Noack volatility and/or kinematic viscosity at 100° C. of a lubricating oil composition, wherein the lubricating oil composition comprises: a base oil mixture, including the $C_{31}$ base oil; one or more performance additives;
wherein the $C_{31}$ base oil is as defined above in an amount of at least 13 wt % based on the total base oil mixture. In particular the use, wherein the resulting lubricating composition has a kinematic viscosity at 100° C. of 9.3 mm$^2$/s or less as measured using ASTM D445; wherein the composition has a Noack volatility of at most 13% as measured using CECL-40-93-B.

BRIEF DESCRIPTION OF THE DRAWINGS

FIG. 1 shows a field ionisation mass spectrometry (FI-MS) analysis of a sample of the $C_{31}$ base oil having more than 60 wt % $C_{31}$ alkanes. The $C_{31}$ base oil (denoted "Isomerised C31 product" in the figure) was obtained by liquid phase catalysed ketonisation of palmitic acid followed by hydrodeoxygenation ("hydrodeoxygenated C31 product") and hydroisomerisation ("Isomerised C31 product") reactions to yield a saturated $C_{31}$ iso-paraffinic material as the $C_{31}$ base oil of FIG. 1.

FIG. 2 shows a FI-MS analysis of the $C_{31}$ base oil according to the present invention (sample I of table 1), where wt-% of paraffins and mono-naphthenes are given as a function of the carbon numbers from 4-72. It can be seen from the figure that the $C_{31}$ base oil has more than 60 wt %, such as more than 80 wt % $C_{31}$ alkanes (paraffins), and that the mono-naphthene amount is small.

FIG. 3 shows a FI-MS analysis of the paraffin content of the $C_{31}$ base oil according to the present invention (all samples A-K of table 1), where wt % of paraffins are given as a function of the carbon numbers from 20-33. It can be seen from FIG. 3A that all the samples of the the $C_{31}$ base oil have more than 80 wt % $C_{31}$ alkanes (paraffins). FIG. 3B is an expansion of FIG. 3A, where the y-axis is shown from 0-5 wt %. It can be seen from FIG. 3B that there is between 1 wt % and 20 wt % $C_{20}$-30 alkanes. Additionally it can be seen that the combined amount of $C_{29}$ and $C_{30}$ alkanes in wt % is less than the combined amount of $C_{26}$ and $C_{27}$ alkanes in wt %.

FIG. 4 shows a FI-MS analysis of the mono-naphthenes content of the $C_{31}$ base oil according to the present invention (all samples A-K of table 1), where wt % of paraffins are given as a function of the carbon numbers from 20-33. It can be seen from FIG. 4 that the amount of mono-naphthenes is low. Further, as mentioned in example 1 there are no other naphthenes present than mono-naphthenes. Additionally it can be seen that each of the amounts of $C_{29}$ and $C_{31}$ cycloalkanes in wt % (as well as the combined amounts of $C_{29}$ and $C_{31}$ mono-naphthenes) more than the sum of the combined amounts of $C_{25}$, $C_{26}$, $C_{27}$, $C_{28}$, $C_{30}$ cycloalkanes.

FIG. 5 shows a combined performance on Noack volatility as a function of the cold cranking simulator viscosity at −30° C. (CCS-30° C.) of a number of low viscosity base oils, including typical API group III oils from Neste Oyj ("NEXBASE group III"), the $C_{31}$ Renewable Base Oil (RBO) of the present invention ("NEXBASE RBO"), typical poly-alpha olefin oils ("PAO typical"), typical Fischer-Tropsch derived base oils (Gas-to-liquid base oils; "GTL") and typical API group III+type paraffinic base oils from hydro-isomerization of hydrocracker bottom oils ("Yubase+"). Both low Noack volatility and low CCS-30° C. viscosity is desirable in low-viscosity base oils. However, as the diagram in FIG. 5 shows there is typically a trade-off between these two properties, in that a low Noack volatility typically results in a high CCS-30° C. viscosity, and conversely that a low CCS-30° C. viscosity typically results in a high Noack volatility. Comparing the $C_{31}$ RBO of the present invention with the other typical low-viscosity base oils, it can be seen that at the same Noack volatility, the other base oils have far higher CCS-30° C. viscosity compared to the $C_{31}$ RBO of the present invention; and that at the same CCS-30° C. viscosities, the $C_{31}$ RBO of the present invention has far lower Noack volatility compared to the other base oils. It can be discerned from FIG. 5 that the $C_{31}$ RBO of the present invention has a far narrower range of Noack volatility (between 5-9 wt %) and CCS-30° C. viscosity (900-1200 mPas) compared to the other low-viscosity base oils, and as such can be considered to be a more well-defined product.

FIG. 6 shows the formulating space for SAE (SAE J300_201501) 0W-30, 0W-20, 0W-16, 0W-12, 0W-8 grades with the High Temperature High Shear (HTHS) and kinematic viscosity at 100° C. (KV100) being two of the important properties of low viscosity SAE grade oils. These two properties have been plotted in FIG. 6 to show that it is possible to obtain the different SAE J300 grades using the $C_{31}$ RBO. The different horizontal lines (dashed/dotted) in the diagram of FIG. 6A shows the minimum HTHS of the SAE grades 30, 20, 16, 12 and 8. The boxes drawn shows the formulating space with respect to HTHS and KV100 for the SAE grades 0W-30, 0W-20, 0W-16, 0W-12, 0W-8 as specified in SAE J300_201501. J300 specifies that the 100° C. kinematic viscosities (KV100) for the same SAE 20, SAE 16, SAE 12, SAE 8 overlap to provide adequate formulating space for these grades. FIG. 6 plots the data of table 6 and shows that the $C_{31}$ RBO may be blended to fit all SAE grades from SAE 0W-20 to SAE 0W-8. FIG. 6 shows a base oil mixture with an additive package, and both with and without any additional viscosity index improver (VII) blended from the $C_{31}$ RBO and NEXBASE® 3035 base oil to obtain a 0W-8 SAE grade base oil mixture. The SAE grades mentioned can be obtained with blends of the $C_{31}$ RBO and NEXBASE® 3035 base oil, where the NEXBASE® 3035 is between 34 wt % and 39 wt % of the unadditized base oil mixture. FIG. 6B is an expansion of the 0W-8 and 0W-12, which also contains the Noack volatility. As evident from FIG. 6B the $C_{31}$ RBO of the present invention can achieve the 0W-8 SAE grade, whereas for example Yubase4+ cannot, and for the 0W-12 SAE grade the $C_{31}$ RBO formulation end up at very similar HTHS and KV100. However, the $C_{31}$ RBO has a significantly better Noack volatility, which translates into a longer time between oil changes due to a lower evaporation loss. Additionally, as shown in table 5, the CCS-35° C. viscosity of the $C_{31}$ RBO 0W-12 SAE grade is also much better than the Yubase4+ 0W-12 SAE grade (3066 mPas vs. 4130 mPas).

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose. While the benefits of the invention have in some instances been described with reference to engine oil for simplification of the discussion, the benefits of the invention are not limited to engine oils. Reference has been made to cycloalkanes and naphthenes. The two terms are intended to cover the same compounds, in the same manner as when reference is being made to alkanes and paraffins.

Base oils for passenger car engines may consist of e.g. 75-90% base oil and 10-25% of a performance enhancing additive package. Since the base oil is typically the largest component in passenger car engines, it has a dramatic effect on the performance of the fluid. The base oil affects many parameters such as the viscosity, oxidation stability, volatility and viscosity index.

Performance enhancing additive packages may include different additives, such as for example antioxidants, metal deactivators, corrosion inhibitors, detergents, dispersants, antiwear additives, friction modifiers, pour point depressants, viscosity improvers, foam inhibitors, thickeners, demulsifiers, emulsifiers, bactericides, fungicides and tackiness additives.

The American Petroleum Institute (API) divides base oils into five main groups. Groups I-III are petroleum base oil of varying qualities.

TABLE 1

API base stock categories

| Group | Sulfur, wt-% | | Saturates, % | Viscosity Index (VI) |
|---|---|---|---|---|
| I | >0.03 | and/or | <90 | 80-119 |
| II | ≤0.03 | and | ≥90 | 80-119 |
| III | ≤0.03 | and | ≥90 | ≥120 |
| IV | Synthetic poly-alpha-olefins (PAOs) | | | |
| V | Any other type of base oil than group I-IV | | | |

The API defines the differences between Group II and III only in terms of the viscosity index (VI), and the Group III base oils are also called very high viscosity base oils (VHVI). However, also cold flow properties as well as Noack volatility number are important characteristics of base oils.

Oil volatility is commonly measured using the Noack volatility test (for example ASTM D5800 or CECL-40-93-B). Prior to the Noack test a lubricant's flash point was used to approximate the oil's volatility. In the Noack test, an oil sample is weighed and heated to 250° C. for one hour (250° C. is intended to simulate upper engine temperatures). Dry air is passed over the sample, carrying the oil vapours that have boiled off and depositing them in a beaker. The original sample is removed and re-weighed. Any reduction in weight is reported as a percentage lost of the original weight. The Noack volatility limit in % weight loss (g/100 g) as measured using ASTM D5800 has to meet standards. The API SN performance classification for example requires weight loss due to volatility to be no greater than 15% for all viscosity grades of motor oil. The lower the Noack number the better, as it is a measure of evaporation of the lightweight molecules in the oil evaporating more readily when exposed to high temperatures, which will reduce the oil level. Low Noack number oils, which resist volatility better can reduce oil consumption and thereby maximise engine performance, when used as engine oil. Most conventional passenger car engine oils of 2016 will typically have Noack volatility numbers of <13 wt % while synthetic passenger car engine oils might be about 9-11 wt %. Full synthetic heavy duty oil can have Noack volatility numbers down to 8-9 wt %.

For base oils, typically it is observed that the higher the boiling range temperature, the higher the viscosity, and the lower the oil volatility. Conversely, it is typically also observed that a lower viscosity is connected to a higher oil volatility.

The higher the oil volatility, the more engine oil evaporates and in turn the heavier the oil becomes. Heavier, more viscous oils circulate poorly, which affects fuel economy, oil consumptions and emissions.

One measure of viscosity is the low temperature cranking viscosity, which is measured by the Cold Crank Simulator viscosity (CCS viscosity) at low temperature, such as for example −30° C. and the value is given in centipoise (cP), which is the same as millipascal-second (mPa*s). It is a test that simulates the action of a starter motor on an engine. The test is important because it is related to the resistance that the battery and starter motor experience when producing an adequate cranking speed at low temperatures, when for example starting an engine during winter time.

The viscosity grade of a lube oil is determined by the Society of Automotive Engineers (SAE). Oils can be separated into multigrade oils and monograde oils. Multigrade oils must fulfill two viscosity specifications, their viscosity grade consists of two numbers, e.g. 10W-40, where 10W refers to the low-temperature viscosity ("Winter"), and 40 refers to the high-temperature viscosity ("Summer").

The SAE low temperature viscosity requirements relating to cranking viscosity specifies that for the 0W SAE viscosity grade, the maximum allowed cranking viscosity is 6200 cP at −35° C. (the lower the value the better). The High Temperature High Shear (HTHS) and kinematic viscosity at 100° C. (KV100) are two of the important properties of the high-temperature viscosity ("Summer") SAE grade of the low viscosity SAE grade oils. The SAE 20, 16, 12 and 8 minimum HTHS are 2.6, 2.3, 2.0 and 1.7 mPas, respectively (SAE J300_201501). J300 specifies that the 100° C. kinematic viscosities (KV100) for the same SAE 20, SAE 16, SAE 12, SAE 8 overlap to provide adequate formulating space for these grades.

One of the objects of the present invention is to provide low viscosity base oils, in particular having both low Noack volatility and low CCS-30° C. viscosity and/or to provide low viscosity base oils at the same time having combination of acceptable HTHS and KV100 to allow the industry's base oil blenders to formulate high quality engine oils, such as SAE grade 0W-20, 0W-16, 0W-12 or 0W-8.

The most important component of a lubricating oil or grease is its base oil. The properties of the base oil may be supplemented by additives. However, it is the base oil that determines the "base" characteristics of the lubricating oil. These characteristics may be modified to a certain extent by the addition of additives.

Most lubricant base oils are mixtures of paraffins (straight- or branched chain hydrocarbons, naphthenes (cycloparaffins), and aromatics (alkyl benzenes and fused ring aromatics). Typically the base oils contain 20-50 carbon atoms per molecule. The base stock may be characterised by its predominant component. Accordingly if paraffins predominate, the base stock is called a paraffinic base oil, if naphthenes predominate, it is a naphthenic base oil, if poly-alpha-olefins (PAO) predominate, it is a PAO base oil. If the base stock is derived from a renewable source, it is a renewable base oil (RBO). For example a PAO base oil derived from a renewable source may be called a renewable PAO base oil, and a paraffinic base oil derived from a renewable source may be called a renewable paraffinic base oil.

The low-viscosity products such as poly-alphaolefin oligomers of 1-decene (for example PAO4), Gas-to-liquids isoparaffin from Fischer-Tropsch synthesis (for example GTL4) and Group III+type paraffinic base oils from hydro-isomerization of hydrocracker bottom (for example Yubase 4 PLUS; Yubase4+) base oils currently have limited availability. These low-viscosity products (~4 cSt), which are needed for formulation of 0W-XX lube oils have limited availability.

The PAO market has historically been constrained by the limited 1-decene availability. Further growth of the GTL market based on natural gas of fossil origin is likely to be limited as future fossil resources are depleted. Such growth considerations can equally be applied to the Group III+type paraffinic base oils from hydro-isomerization of hydrocracker bottom.

Accordingly there is a need for further low-viscosity base oil products, in particular products that are not constrained by limited olefin availability or potential future depletion of fossil resources.

The $C_{31}$ Base Oil

The present invention is based on the novel $C_{31}$ base oils having more than 60 wt % $C_{31}$ alkanes, which may form part of the lubricating oil compositions of the present invention as well as forming part of the base oil mixtures of the present invention to obtain low viscosity base oils, in particular having both low Noack volatility and low CCS viscosity (such as CCS-30° C., CCS-35° C. and CCS-40° C.) and/or to provide low viscosity base oils at the same time having combination of acceptable HTHS and KV100 to allow the industry's base oil blenders to formulate high quality engine oils, such as SAE grade 0W-20, 0W-16, 0W-12 or 0W-8.

Unless otherwise mentioned, the weight percentages of the hydrocarbons have been measured using field ionisation mass spectrometry (FI-MS), for example as described in the examples.

In the present description and claims reference is made to "$C_{31}$ base oil" and "$C_{31}$ renewable base oil" are used interchangeably. However, the base oil composition is preferably of renewable origin. The renewable character of the fatty acid feedstock for the renewable base oil of the present invention provides for a stronger security of supply to the industry's base oil blenders (OEMs). The renewable content may also be determined by isotopic distribution involving $^{14}C$, $^{13}C$ and/or $^{12}C$ as described in ASTM D6866.

The $C_{31}$ base oil is a paraffinic base oil, which comprises more than 60 wt % $C_{31}$ alkanes. The $C_{31}$ base oil can be manufactured from a saturated $C_{16}$ fatty acid (palmitic acid) through ketonisation, hydrodeoxygenation (HDO) and hydroisomerisation reactions. Typically the reaction ketonisation reaction of palmitic acid will precede the HDO and ISOM reactions as described in example 1, but other variants can also be used, such as hydroisomerisation of palmitic acid followed by ketonisation and HDO reactions.

Without wishing to be bound to any particular theory, it is speculated by the inventors that the superior qualities of the $C_{31}$ base oil of the present invention is obtained from a liquid phase ketonisation reaction (as opposed to a gas phase ketonisation reaction) of palmitic acid having 16 carbon atoms. The single carbon number fatty acid in combination with liquid phase ketonisation (followed by HDO and hydroisomerisation) was surprisingly found to give almost exclusively the $C_{31}$ base oil without the expected amounts of the lower homologues ($C_{30}$, $C_{29}$, $C_{28}$, $C_{27}$, $C_{26}$, etc.) which is common for (gas phase) ketonisation, hydrodeoxygenation and hydroisomerisation reactions. Reference is made to FIG. 3A showing almost exclusively (80 wt % to 95 wt %) $C_{31}$ paraffinic base oil, with no multi-ring naphthenes, and very low amounts of mono-naphthenes. See FIG. 4 and table 1, where it can be seen that the total naphthenes as well as the total mono-naphthenes are certainly below 9.0 wt %, such as below 4.5 wt %, and in many cases below 4.0 wt %.

It is primarily the $C_{31}$ paraffinicity of the $C_{31}$ base oil that separates the novel oil from many other paraffinic base oils. This paraffinicity is obtained by ketonising a feedstock that is exclusively or highly enriched in $C_{16}$ saturated fatty acid (palmitic acid). A particularly well-suited raw material for palmitic acid is palm oil fatty acid distillate (PFAD), which comprises degraded fats that are unsuited for food production and need to be removed during the palm oil refining process before the palm oil meets the food industry's quality standards. The fatty acid composition of PFAD varies by source, but some mean value of fatty acids in PFAD of different oil processing industries in Pakistan was found (Chang et al. (2016, J. Oleo. Sci. 65(11), 897-901) to be: 0.04% C12:0; 0.42% C14:0; 41.25% C16:0; 7.29% C18:0; 41.58% C18:1; 8.95% C18:2; 0.04% C20:1; 0.27% C20:1; 0.07% C22:0; and 0.05% C24:0.

Accordingly, PFAD may be comprised of:
0.46% $C_{12}$-$C_{14}$ fatty acids,
41.25% palmitic acid,
57.82% $C_{18}$ fatty acids, and
0.43% $C_{20}$-$C_{24}$ fatty acids.

The separation of palmitic acid from higher boiling fatty acids on a large scale is not a simple matter, as palmitic acid has a boiling point of 351° C., stearic acid at 361° C. By conducting a reduced pressure fractional distillation as described in example 1, it was possible to obtain palmitic acid with a purity of 99.72 wt % and 98.66 wt %, which makes the invention commercially feasible on a large industrial scale (e.g. more than 1000 t/annum) as opposed to laboratory scale.

The purity described above for palmitic acid can be converted into a $C_{31}$ base oil comprising more than 80 wt % $C_{31}$ alkanes and higher such as up to 95 wt % $C_{31}$ alkanes. Different feedstocks than PFAD and variations in e.g. PFAD composition as well as distillation efficiency could result in a base oil, where the $C_{31}$ base oil comprises more than 60 wt % $C_{31}$ alkanes, such as more than 70 wt % $C_{31}$ alkanes, which still possesses at least some of the superior properties provided. It is preferred that the $C_{31}$ content is more than 70 wt %, and as also evident from FIG. 3A more than 80 wt % $C_{31}$ alkanes, for example between 60 wt % and 95 wt % $C_{31}$ alkanes.

Should the palmitic acid be less pure than in example 1, there could be a situation, where the $C_{31}$ base oil comprises up to 20 wt % of $C_{32}$ or higher alkanes. $C_{32}$ or higher includes $C_{32}$ to $C_{46}$, such as $C_{32}$ to $C_{35}$ which would be the resulting range for a palmitic acid with $C_{18}$ fatty acid impurities. It is desired that the level of impurities should be low, and in any event the $C_{31}$ base oil should have less than 20 wt % $C_{32}$ or higher alkanes, preferably less than 10 wt % $C_{32}$ or higher alkanes. This is also what is obtained with the palmitic acid of example 1, where the resulting $C_{31}$ base oils have less than 5 wt %, and even less than 1 wt % $C_{32}$ or higher alkanes as evident from table 1, FIGS. 2 and 3B.

Without wishing to be bound by any specific theory, it is speculated by the inventors that the liquid phase ketonisation reaction as opposed to a gas phase ketonisation reaction of palmitic acid having 16 carbon atoms also results in the low amounts of naphthenes. Accordingly, the $C_{31}$ base oil will have less than 9 wt % cycloalkanes, preferably less than 4.5 wt % cycloalkanes as also evident from the mono-naphthenes amounts shown in table 1 and FIG. 4. For example less than 8 wt % $C_{25}$-32 cycloalkanes (i.e. comprising mono-naphthenes, di-, tri-, tetra-, penta-hexa- and higher naphthenes) or less than 4.5 wt % $C_{25}$-32 cycloalkanes;

Finally, it is important that the $C_{31}$ base oil is highly iso-paraffinic, meaning that the alkanes of the base oil should comprise 70 wt % or more iso-alkanes, for example 80 wt % or more, even as high as 90 wt % or more, 95 wt % or more or 99 wt % or more. There are many different iso-alkanes ranging from a single methyl-branched $C_{31}$ base oil to more highly branched $C_{31}$ base oils. The degree of branching of the iso-alkanes correlates with the pour point of the resulting isomerised $C_{31}$ base oil. The degree of isomerisation may therefore also be given for the $C_{31}$ base oils of the present invention in a functional manner by specifying the pour point. In particular during the hydroisomerisation reactions the extent of isomerisation is often run until a particular desired pour point is obtained. The degree of isomerisation can therefore be given as the amount of iso-alkanes in wt % or as a pour point of the $C_{31}$ base oil, or preferably as a combination of the amount of iso-alkanes and pour point. For example the pour point of the $C_{31}$ base oil may be less than −5° C. as measured using ASTM D7346, such as less than −10° C. or less than −15° C., or even as high as less than −19° C. or less than −25° C. as provided in example 1 and shown in table 2. As there is some loss of the $C_{31}$ base oil during the hydroisomerisation reactions due to cracking, there is often a compromise between $C_{31}$ base oil yield and degree of isomerisation such that the pour point is between −5° C. to −35° C., such as between −10° C. to −30° C.

Due to the starting material being almost exclusively palmitic acid, the ketonisation reaction type and the degree of isomerisation as described above, the $C_{31}$ base oil composition contains very little cracked product, which typically results in higher Noack volatility values. Therefore the $C_{31}$ base oil composition may be further characterised in that it comprises low amounts of $C_{20}$-30 alkanes, in that it may comprise between 1 wt % and 15 wt % $C_{20}$-30 alkanes as evident from the results provided in table 1 and FIGS. 2 and 3B, for example less than 30 wt %, such as less than 20 wt %, or less than 15 wt % $C_{20}$-30 alkanes, such as less than 10 wt % $C_{20}$-30 alkanes, or even as low as less than 7 wt % $C_{20}$-30 alkanes.

The particular method of preparing the $C_{31}$ base oil as described in example 1, involving obtaining the palmitic acid from PFAD, the liquid phase ketonisation reaction, hydrodeoxygenation and hydroisomerisation provides the $C_{31}$ base oil composition with at least two "finger-print" identifiers, which can be used for identification of the particular method and feed used. Accordingly, the base oil composition may be further characterised by a first "finger-print" identifier in that the amount of $C_{29}$ and/or $C_{30}$ alkanes in wt % is less than the combined amount of $C_{26}$ and $C_{27}$ alkanes in wt %, which can be seen from FIG. 3B.

The $C_{31}$ base oil composition may additionally be characterised by a second "finger-print" identifier, where the combined amount of $C_{29}$ and $C_{31}$ cycloalkanes in wt % being more than the combined amounts of $C_{25}$, $C_{26}$, $C_{27}$, $C_{28}$, $C_{30}$ cycloalkanes, which can be seen from FIG. 4.

As described herein, preferably the $C_{31}$ base oil is of renewable origin, which in addition to providing a stronger security of supply to the to the industry's base oil blenders, also provides with distinct advantages compared to e.g. base oils of fossil origin, in that the $C_{31}$ base oil has very little impurities.

In particular the base oil composition is mainly paraffinic with few and low amounts of impurities. Accordingly, the renewable base oil composition may be further characterised in that at least one or more (but preferably all) of impurities—if present—are:
  less than 1.5 wt % aromatic hydrocarbons, preferably less than 0.5 wt % such as less than 0.3 wt %, for example 0.1 wt % or less;
  less than 1.0 wt % di-, tri-, tetra-naphthenes, or higher, preferably less than 0.5 wt %;
  less than 1 wt % of oxygen-containing compounds, preferably less than 0.5 wt %, such as less than 0.3 wt %, for example 0.1 wt % or less;
  less than 300 ppm sulfur, such as less than 100 ppm or less than 50 ppm, such as less than 1 ppm sulfur content as measured using ASTM D 3120;
  less than 100 ppm nitrogen or less than 10 ppm nitrogen, such as less than 1 ppm nitrogen content as measured using ASTM D 4629.

The $C_{31}$ base oil compositions may further be functionally characterised by having one or more of the following properties:
  a boiling point of between 350° C. and 650° C. as measured using ASTM D7500;
  a viscosity index (VI) of more than 140 as measured using ASTM D2270
  a Noack volatility number of less than 10 wt % as measured using ASTM D5800 or CECL-40-93-B;
  a pour point of less than −10° C. as measured using ASTM D7346;
  a Cold-Cranking Simulator (CCS-35° C.) viscosity of less than 1800 mPas as measured using ASTM D5293;
  a Cold-Cranking Simulator (CCS-30° C.) viscosity of less than 1300 mPas as measured using ASTM D5293;
  a kinematic viscosity (KV100) of less than 5 mm$^2$/s using EN ISO 3104.

The base oil compositions may further be functionally characterised by having a boiling point above 380° C. as measured using ASTM D7500, such as having a boiling point above 420° C. as measured using ASTM D7500. The base oil compositions may further be functionally characterised by having a boiling point below 650° C., such as below 600° C. In some cases the boiling point above is defined as the 5% boiling point of ASTM D7500. For example the boiling point ranges of the $C_{31}$ base oil may be 380-650° C., 400-620° C., 420-600° C. measured either as the range between the initial boiling point (IBP) and the final boiling point (FBP) or between the 5% and 95% distillation points The distillation range for the $C_{31}$ base oil is narrow. For example more than 30% of the sample may boil within a temperature range of 10° C. (e.g. the values of the 50% and 90% boiling points of ASTM D7500 being only 10° C. apart), or having a boiling point range between the values of the 10% and 90% boiling points of ASTM D7500 boiling within a temperature range of less than 70° C., for example less than 50° C., such as less than 40° C.

The combined performance of low Noack volatility values in combination with the low CCS-30° C. viscosities of the $C_{31}$ base oil is another parameter in which the $C_{31}$ base oil distinguishes itself from other low-viscosity base oils. Both low Noack volatility and low CCS-30° C. viscosity is desirable in low-viscosity base oils. However, as the diagram in FIG. 5 shows there is typically a trade-off between these two properties, in that a low Noack volatility typically results in a high CCS-30° C. viscosity, and conversely that a low CCS-30° C. viscosity typically results in a high Noack volatility. Comparing the $C_{31}$ RBO of the present invention with the other typical low-viscosity base oils, it can be seen that at the same Noack volatility, the other base oils have far higher CCS-30° C. viscosities compared to the $C_{31}$ RBO of the present invention; and that at the same CCS-30° C. viscosities, the $C_{31}$ RBO of the present invention has far lower Noack volatility compared to the other base oils. It can be discerned from FIG. 5 that the $C_{31}$ RBO of the present invention has a far narrower range of Noack volatility (between 5-9 wt %) and CCS-30° C. viscosity (900-1200 mPas) compared to the other low-viscosity base oils, and as such can be considered to be a more well-defined product.

Accordingly, the $C_{31}$ base oil compositions may further be functionally characterised by having both the properties of:
  a Noack volatility number of less than 10 wt %, such as less than 9 wt % as measured using ASTM D5800 or CECL-40-93-B; and a Cold-Cranking Simulator (CCS-30° C.) viscosity of less than 1600 mPas, such as less than 1300 mPas as measured using ASTM D5293;

In particular the combination between low Noack volatility and low CCS-30° C. viscosity is a property of the $C_{31}$ base oil of the present invention. In particular combinations of CCS-30° C. viscosity between 700-1300 mPas together with Noack volatility between 5-10 wt %, such as combinations of CCS-30° C. viscosity between 700-1200 mPas together with Noack volatility between 5-9 wt %, such as combinations of CCS-30° C. viscosity between 800-1100 mPas together with Noack volatility between 6-9 wt %, such as combinations of CCS-30° C. viscosity between 800-1050 mPas together with Noack volatility between 6.5-9 wt % for example in relation to FIG. 5, combinations of CCS-30° C. viscosity lower than 1400 mPas together with Noack volatility lower than 10 wt %, such as combinations of CCS-30° C. viscosity lower than 1300 mPas together with Noack volatility lower than 9.5 wt %.

The $C_{31}$ base oil composition may in addition to the Noack volatility and CCS-30° C. viscosity be functionally characterised by:
a kinematic viscosity (KV100) of less than 5 mm²/s using EN ISO 3104.

The base oil compositions may also be functionally characterised by having one or more of the following properties:
a Noack volatility number of less than 10 wt % as measured using ASTM D5800 or CECL-40-93-B; and
a kinematic viscosity (KV100) of less than 5 mm²/s using EN ISO 3104.

Base oil mixtures comprising the $C_{31}$ base oil

As described herein the $C_{31}$ base oil have attractive properties with respect to low viscosity and low Noack volatility. Such properties may advantageously be utilised in the blending of a base oil mixture, such as a base oil mixture for an internal combustion engine. As the base oil is typically the largest component in passenger car engines, it has a dramatic effect on the performance of the fluid. The base oil affects many parameters such as the viscosity, oxidation stability, volatility and viscosity index. The availability of the novel $C_{31}$ base oil provides for the possibility to obtain SAE grade specifications by using less additive package or alternatively by using less or no amount of other known low viscosity oils.

The $C_{31}$ base oil composition of the present invention may be part of a base oil mixture with other base oils. A base oil mixture, for example a base oil mixture for internal combustion engines comprising at least 13 wt % of the $C_{31}$ base oil as defined above; the remainder selected from one or more base oils in the same or in different API (American Petroleum Institute) category; wherein the amounts given in wt % are based on the total base oil mixture.

The $C_{31}$ base oil amount of the base oil mixture may be present in an amount of at least 35 wt % based on the total base oil mixture, such as in an amount of at least 50 wt % based on the total base oil mixture. The $C_{31}$ base oil may for example be at least 60 wt % based on the total base oil mixture as shown in tables 3, 5 and 6, such as at least 80 wt % based on the total base oil mixture, and up to 95 wt % or even 100 wt % based on the total base oil mixture may be the $C_{31}$ base oil. The base oil mixture may have a content of the $C_{31}$ base oil of the present invention of between 15-100 wt %, such as between 15-95 wt %, for example between 20-90 wt % based on the total base oil mixture.

The base oil mixture may in addition to the at least 13 wt % of a renewable base oil, comprise two or more base oils in the same or different API category. For example the base oil mixture may comprise 10-87 wt % based on the total base oil mixture of a Group II and/or Group III base oil, for example less than 50 wt % or less than 40 wt % based on the total base oil mixture of a Group II and/or Group III base oil.

As shown in e.g. tables 2 and FIGS. 5 and 6 the $C_{31}$ base oil has properties that are comparable as well as superior to the properties of other low-viscosity base oils, such as polyalphaolefins (PAOs) or Fischer-Tropsch derived base oils (GTLs).

This provides for the possibility that less poly-alphaolefin (PAO) or even the absence of PAO in base oil mixtures for low-viscosity lubricating oils. For example the base oil mixture may contain no more than 10 wt % of a polyalphaolefin base oil, or the base oil mixture may be essentially free of polyalphaolefin base oil, preferably wherein the base oil mixture is free of polyalphaolefin base oil. Essentially free of poly-alphaolefin base oil can be considered as the content being 2 wt % or less.

This provides for the possibility that less Fischer-Tropsch derived base oil (GTL) or even the absence of GTL in base oil mixtures for low-viscosity lubricating oils. For example the base oil mixture may contain no more than 10 wt % of a Fischer-Tropsch derived base oil. For example, the base oil mixture may be essentially free of Fischer-Tropsch derived base oil, preferably wherein the base oil mixture is free of Fischer-Tropsch derived base oil. Essentially free of Fischer-Tropsch derived base oil can be considered as the content being 2 wt % or less.

Lubricating Oil Compositions Comprising the $C_{31}$ Base Oil

As described herein the $C_{31}$ base oil have attractive properties with respect to low viscosity and low Noack volatility. Such properties may advantageously be utilised in the blending of a base oil mixture and in lubricant formulations comprising such base oil mixtures together with an additive package, e.g. a base oil mixture and lubricating oil composition for an internal combustion engine. As the base oil is typically the largest component in passenger car engines, it has a dramatic effect on the performance of the fluid. The base oil affects many parameters such as the viscosity, oxidation stability, volatility and viscosity index. The availability of the novel $C_{31}$ base oil provides for the possibility to obtain SAE grade specifications in lubricating oil compositions by using less additive package or alternatively by using less or no amount of other known low viscosity oils.

Lubricating oil compositions, for example lubricating oil compositions for internal combustion engines comprises: a) a base oil mixture comprising at least 13 wt % of a $C_{31}$ base oil; the remainder selected from one or more base oils in the same or different API (American Petroleum Institute) category; wherein the amounts of base oils given in wt % are based on the total base oil mixture; b) one or more performance additives.

The composition of the $C_{31}$ base oil is as described in the present specification, comprising for example more than 60 wt % $C_{31}$ alkanes, preferably more than 80 wt % $C_{31}$ alkanes; wherein the amounts of renewable base oil is given in wt % based on the renewable base oil; the weight percentages of the hydrocarbon composition of the renewable base oil may be measured using field ionisation mass spectrometry (FI-MS). Reference is made to the section titled "The $C_{31}$ base oil" for further detailed information about the structure and properties of the $C_{31}$ base oil. Reference is additionally made to the section "Base oil mixtures comprising the $C_{31}$ base oil" for further detailed information about the composition of the base oil mixture. To avoid repetition, the features from these two sections have not been repeated in this section as it is clear that the features of those sections should be consulted in relation to further specifying the features of the base oil mixture and $C_{31}$ base oil composition in the lubricating oil compositions of the present invention.

As mentioned in the summary of the invention it has been found that that including the $C_{31}$ (renewable) base oil obtainable from the $C_{16}$ fatty acids present in palm oil and other (renewable) feedstocks has superior properties in relation to both low Noack volatility and low CCS-30° C. viscosity (FIG. 5) as well as having a combination of acceptable HTHS and KV100 to allow the industry's base oil blenders to formulate high quality engine oils, such as SAE grade 0W-20, 0W-16, 0W-12 or 0W-8 (FIG. 6).

Additionally, the renewable character of the fatty acid feedstock for the renewable base oil of the present invention provides for a stronger security of supply to the industry's base oil blenders compared to base oils that could be constrained by limited olefin availability or by a potential future depletion of fossil resources.

The lubricating oil composition comprises a base oil mixture and an additive package. The base oil mixture comprises the $C_{31}$ base oil.

The reason that an additive package is often needed for the formulation of lubricating oil compositions is because the base oils alone often do not meet the requirements of modern lubricating oils and greases. Additives are chemical substances added to the base oil to impart or improve certain properties. Additives include at least one or more of the performance additives of the lubricating oil composition may be selected from the list consisting of: antioxidants, metal deactivators, corrosion inhibitors, detergents, dispersants, antiwear additives, friction modifiers, pour point depressants, viscosity improvers, foam inhibitors, thickeners demulsifiers, emulsifiers, bactericides, fungicides and tackiness additives. Additives that have more than one function/property are called multipurpose additives.

The individual performance additives may result in additive effects, synergistic effects or antagonistic effects, and often an additive package comprising a number of different performance additives is developed and added to the base oil mixture to produce the lubricating oil composition with the desired characteristics.

When designing lubricating oil compositions it is these additives and base oils that are the key elements for obtaining the increasingly demanding requirements of equipment manufacturers and users of lubricating oils and greases.

As the person skilled in the art is familiar with the above additive types and other additives, these are not further discussed here in detail. Specific examples of such additives are described in for example Gresham, R. M., Canter, N. M., Zabawski, E. S. and Zou, M. 2015. Lubrication and Lubricants. Kirk-Othmer Encyclopedia of Chemical Technology. 1-77.

The $C_{31}$ base oil composition properties allows the lubricating oil composition to be formulated to meet the specifications for 0W-XX, such as any one of 0W-20, 0W-16, 0W-12, or 0W-8, see FIG. 6A. The $C_{31}$ renewable base oil allows formulation of very low-viscosity grades meeting the specifications for 0W-12, or meeting the specifications for 0W-8. Reference is made to FIG. 6B, which is an expansion of the 0W-8 and 0W-12 formulating spaces of FIG. 6A, which also shows the individual Noack volatilities. As evident from FIG. 6B the $C_{31}$ RBO of the present invention can achieve the 0W-8 SAE grade, whereas for example Yubase4+ cannot, and for the 0W-12 SAE grade the $C_{13}$ RBO formulation end up at very similar HTHS and KV100. However, the $C_{31}$ RBO has a significantly better Noack volatility, which translates into a longer time between oil changes due to a lower evaporation loss. Additionally, as shown in table 5, the CCS-35° C. viscosity of the $C_{31}$ RBO 0W-12 SAE grade is also much better than the Yubase4+ 0W-12 SAE grade (3066 mPas vs. 4130 mPas).

As shown in FIG. 6B, the 0W-8 SAE grade is achievable with the $C_{31}$ base oil, when it is mixed with NEXBASE® 3035, which is a lower cost standard API group II quality having low viscosity and high Noack volatility.

When formulating lubricating oil compositions it is desirable to use lower cost or standard API group II base oils to reduce the cost of the resulting lubricating oil, and mix these base oils with other low-viscosity oils, such as high performance and more expensive oils, such as Yubase4+. However, the use of products like NEXBASE® 3035 is difficult, or almost impossible, with products like Yubase4+ because the lubricating oil composition would end up in a too high Noack volatility as the Noack of Yubase4+ formulation is already on the high side (see table 2) without the addition of NEXBASE® 3035, which is an example of a standard API ground II base oil having a rather high Noack volatility of about 23 wt %.

The low Noack volatility as well as the low CCS viscosity of the $C_{31}$ base oil of the present invention provides the formulators of base oil mixtures and lubricating oil compositions with a new degree of freedom, in that they can start to use products which were previously considered to be technically abandoned for the lower SAE 0W-XX grades due to a (too) high Noack volatility. These technically abandoned and higher Noack volatility base oils can now be used to provide base oil mixtures and lubricating oil compositions together with the $C_{31}$ base oil of the present invention and still meet the Noack requirements (e.g. the requirement of a Noack volatility of 13 wt % or less for ACEA passenger car motor oil grades (PCMO)). NEXBASE® 3035 is an example of such a product with Noack about 23 wt %, which was difficult to use with the low viscosity oils (e.g. the PAOs, GTLs Yubase+ mentioned in table 2, all having close to 13 wt % Noack volatility) needed to reach the lower SAE 0W-XX grades, such as 0W-12 and 0W-8, and still meet the requirement of a Noack volatility of 13 wt % or less for ACEA PCMO. Reference is made to FIG. 6B and entry B4 of table 5, which shows that the $C_{31}$ base oil enables a blended base oil mixture containing a substantial amount (34 wt %) of NEXBASE® 3035 and still have an acceptable Noack volatility of 12.4 wt % in a SAE grade 0W-8 oil.

Due to the superior properties of the $C_{31}$ base oil with regards to both Noack volatility and kinematic viscosity the $C_{31}$ base oil according to the present invention can be used for reducing the Noack volatility and/or kinematic viscosity at 100° C. of a lubricating oil composition, wherein the lubricating oil composition comprises:
 a base oil mixture, including the $C_{31}$ base oil;
 one or more performance additives;
wherein the $C_{31}$ base oil is as defined above in an amount of at least 13 wt % based on the total base oil mixture.

In particular the use, wherein the resulting lubricating composition has a kinematic viscosity at 100° C. of 9.3 mm$^2$/s or less as measured using ASTM D445; and wherein the composition has a Noack volatility of at most 13% as measured using CECL-40-93-B.

Due to the superior properties of the $C_{31}$ base oil with regards to both Noack volatility and Cold Cranking simulator viscosity, the $C_{31}$ base oil according to the present invention can be used for reducing the Noack volatility and/or cold cranking simulator viscosity (e.g. at −30° C., −35° C. or −40° C.) of a lubricating oil composition, wherein the lubricating oil composition comprises:
- a base oil mixture, including the $C_{31}$ base oil;
- one or more performance additives;

wherein the $C_{31}$ base oil is as defined above in an amount of at least 13 wt % based on the total base oil mixture.

In particular the use, wherein the resulting lubricating composition has CCS-35° C. viscosity of less than 4000 mPas; and wherein the composition has a Noack volatility of at most 13% as measured using CECL-40-93-B Due to the superior properties of the $C_{31}$ base oil with regards to both kinematic viscosity and high temperature high shear (HTHS) the $C_{31}$ base oil according to the present invention can be used for reducing the kinematic viscosity at 100° C. and/or HTHS of a lubricating oil composition, wherein the lubricating oil composition comprises:
- a base oil mixture, including the $C_{31}$ base oil;
- one or more performance additives;

wherein the $C_{31}$ base oil is as defined above in an amount of at least 13 wt % based on the total base oil mixture.

In particular the use, wherein the composition has a HTHS at 150° C. of between 1.70 and 2.90 m Pas, such as between 1.70 and 2.00 m Pas or between 2.00 and 2.30 mPas; and wherein the resulting lubricating composition has a kinematic viscosity at 100° C. of 9.3 mm²/s or less, such as 8.2 mm²/s or less, such as 7.1 mm²/s or less, such as 6.1 mm²/s or less as measured using ASTM D445

The weight percentages of the hydrocarbon composition of the renewable base oil may be measured using field ionisation mass spectrometry (FI-MS). Such methods as well as other methods are known to the skilled person. For example the the FI-MS method has been described in the examples section, which also makes reference to Jin et al. *"Comparison of Atmospheric Pressure Chemical Ionization and Field Ionization Mass Spectrometry for the Analysis of Large Saturated Hydrocarbons" Anal. Chem.* 2016, 88(21) 10592-10598, where the method has also been described and compared together with other methods. In preferable embodiments the weight percentages of the hydrocarbon composition of the renewable base oil may be measured using field ionisation mass spectrometry (FI-MS), in particular the paraffinic amounts and the naphthenic amounts.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

Example 1—Preparing a $C_{31}$ renewable base oil from a palmitic acid feed

Palmitic acid was isolated by distillation of palm fatty acid distillate (PFAD) at a temperature of about 250-275° C. and at 0.01-0.05 barg pressure. A first sample of palmitic acid starting material was 99.72 wt % pure with minor impurities of: $C_{14}$ fatty acids (0.07 wt %) and $C_{15}$ fatty acids (0.06 wt %). A second sample of palmitic acid starting material was 98.66 wt % pure with minor impurities of: $C_{18}$ fatty acids (0.42 wt %); $C_{14}$ fatty acids (0.07 wt %); $C_{15}$ fatty acids (0.07 wt %). The second sample was used in the rest of the example.

Palmitic acid was fed to a fixed bed reactor operated in continuous mode comprising a catalyst bed loaded with 250 g catalyst material (TiO2 BET 50-54 m²/g; average pore size 100-200 Å; crystallinity 50-100%). The ketonisatisation was conducted in the liquid phase at a pressure of about 18 bar, temperature of about 360° C., WHSV of about 1.0 h⁻¹, and an extra gas flow of 131 l/h nitrogen. The ketonisation reaction was stopped at around 82-87% fatty acid conversion.

The resulting ketonised product was hydrodeoxygenated over a NiMo/Al$_2$O$_3$ catalyst at a temperature of about 310° C., a pressure of about 40 bar, a WHSV of about 1.5 h⁻¹, and H2/feed oil ratio of 900 nl/l to yield a hydrodeoxygenated product (see exemplary GC-FID response in FIG. 1). The efficiency of oxygen removal was 99.9% for the HDO step.

The resulting hydrodeoxygenated product was hydroisomerised over a platinum impregnated zeolite as the hydroisomerisation catalyst with at temperatures of about 300-350° C., a pressure of about 20-40 bar, and at a WHSV of about 0.8-1.0 h⁻¹ to yield hydroisomerised products A-K (see exemplary GC FID response in FIG. 1).

The hydroisomerised product is fractionated, and the 380+° C. fraction is isolated as a renewable base oil product.

The composition of the renewable base oil product is analysed using field ionisation mass spectrometry (FI-MS) analysis, see table 1 ("The FIMS method").

No di-, tri-, tetra, penta-hexa-naphthenes were detected. No aromatic compounds were detected.

The distillation range as measured using ASTM D7500 for sample I was: IBP (355° C.); 5% (395° C.); 10% (421° C.); 20% (435° C.); 30% (440° C.); 40% (443° C.); 50% (445° C.); 60% (448° C.); 70% (450° C.); 80% (452° C.); 90% (454° C.); 95% (456° C.); FBP (583° C.).

Field ionisation mass spectrometry (FI-MS).

Prior to the FI-MS analysis, any aromatic content is separated from the saturated fraction, and both fractions are analysed separately using FIMS.

In the FI-MS method, saturated hydrocarbons are classified according to the below molecular weights based on carbon and hydrogen atoms by field ionization mass spectrometry (FI-MS) as follows:

$C_nH_{2n+2}$ are classified as paraffins;
$C_nH_{2n}$ are classified as mono-naphthenes;
$C_nH_{2n-2}$ are classified as di-naphthenes;
$C_nH_{2n-4}$ are classified as tri-naphthenes;
$C_nH_{2n-6}$ are classified as tetra-naphthenes;
$C_nH_{2n-8}$ are classified as penta-naphthenes;
$C_nH_{2n-10}$ are classified as hexa-naphthenes.

All FI mass spectra were obtained in centroid mode using a Thermo Fisher Scientific double focusing sector (DFS) mass spectrometer equipped with a liquid injection field desorption ionization (LIFDI, Linden ChroMasSpec GmbH) source that was operated in FI mode. DFS MS was operated in the magnetic scan mode at a resolution of 2 000 (±50). Ion source parameters were as follows: acceleration voltage, +5 kV; counter electrode voltage, −5 kV; reference inlet temperature, 80° C.; ion source temperature, 50° C.; flash duration, 150 ms; and interscan delay, 150 ms. Two types of FI emitters were used: Linden ChroMasSpec GmbH FI-emitter 10 μm, 20 mA type at 50 mA and CarboTec 10 μm Allround emitter at 90 mA. New emitters were preconditioned before the sample runs by applying emitter heating current for 2 h. DFS MS was scanned from m/z 50 up to 1000 at the rate of 7.5 s/decay. The direct insertion probe (DIP) was heated during the experiment from 50° C. up to 360° C. at a ramp rate of 25° C./min. A volume of 2 μL of sample solution was injected into a sample holder (crucible, Mascom GmbH 0568770S-0568780S for low viscosity base oils and Mascom GmbH 0568760S for other base oils and model compound mixtures) and the solvent was allowed to evaporate at room temperature prior to analysis. The sample holder was placed into a DIP and introduced into the ion source via a vacuum exchange lock. The sample run was started immediately after the sample was introduced into the ion source. Xcalibur 2.2 program (Thermo Fisher Scientific, Inc., San Jose, Calif.) was used for acquisition and analysis of the MS data.

The method has also been described in Jin et al. "*Comparison of Atmospheric Pressure Chemical Ionization and Field Ionization Mass Spectrometry for the Analysis of Large Saturated Hydrocarbons*" Anal. Chem. 2016, 88(21) 10592-10598.

TABLE 1

FIMS result of RBO product 380+° C. cut

| Carbon number | A | B | C | D | E |
|---|---|---|---|---|---|
| Paraffins (wt %) | | | | | |
| 20 | 0.09 | 0.05 | 0.00 | 0.00 | 0.10 |
| 21 | 0.14 | 0.08 | 0.05 | 0.00 | 0.16 |
| 22 | 0.22 | 0.19 | 0.18 | 0.00 | 0.23 |
| 23 | 0.48 | 0.29 | 0.22 | 0.08 | 0.38 |
| 24 | 0.89 | 0.46 | 0.46 | 0.31 | 0.69 |
| 25 | 1.13 | 0.43 | 0.54 | 0.76 | 0.95 |
| 26 | 1.16 | 0.89 | 0.63 | 1.23 | 1.20 |
| 27 | 1.83 | 1.20 | 0.80 | 2.06 | 1.67 |
| 28 | 0.57 | 0.33 | 0.27 | 0.61 | 0.46 |
| 29 | 0.20 | 0.13 | 0.24 | 0.33 | 0.19 |
| 30 | 0.22 | 0.18 | 0.00 | 0.27 | 0.23 |
| 31 | 89.19 | 91.60 | 92.96 | 89.97 | 89.84 |
| 32 | 0.13 | 0.20 | 0.00 | 0.17 | 0.13 |
| 33 | 0.00 | 0.10 | 0.08 | 0.10 | 0.09 |
| Total paraffins | 96.3 | 96.1 | 96.4 | 95.9 | 96.3 |
| Mononaphthenes (wt %) | | | | | |
| 21 | 0.00 | 0.00 | 0.00 | 0.00 | 0.00 |
| 22 | 0.00 | 0.00 | 0.00 | 0.00 | 0.00 |
| 23 | 0.00 | 0.00 | 0.00 | 0.00 | 0.00 |
| 24 | 0.00 | 0.00 | 0.00 | 0.00 | 0.00 |
| 25 | 0.00 | 0.00 | 0.00 | 0.00 | 0.00 |
| 26 | 0.00 | 0.07 | 0.09 | 0.06 | 0.00 |
| 27 | 0.10 | 0.15 | 0.00 | 0.25 | 0.13 |
| 28 | 0.20 | 0.30 | 0.24 | 0.23 | 0.13 |
| 29 | 1.63 | 1.29 | 1.25 | 0.98 | 1.09 |
| 30 | 0.00 | 0.00 | 0.00 | 0.12 | 0.00 |

TABLE 1-continued

FIMS result of RBO product 380+° C. cut

| | | | | | |
|---|---|---|---|---|---|
| 31 | 1.81 | 1.97 | 1.99 | 2.48 | 2.33 |
| 32 | 0.00 | 0.10 | 0.00 | 0.00 | 0.00 |
| 33 | 0.00 | 0.00 | 0.00 | 0.00 | 0.00 |
| Total mononapht. | 3.7 | 3.9 | 3.6 | 4.1 | 3.7 |

| Carbon number | F | G | H | I | J | K |
|---|---|---|---|---|---|---|
| Paraffins (wt %) | | | | | | |
| 20 | 0.00 | 0.00 | 0.00 | 0.00 | 0.00 | 0.00 |
| 21 | 0.00 | 0.00 | 0.00 | 0.15 | 0.00 | 0.00 |
| 22 | 0.11 | 0.00 | 0.00 | 0.32 | 0.00 | 0.00 |
| 23 | 0.25 | 0.19 | 0.22 | 0.83 | 0.00 | 0.00 |
| 24 | 0.60 | 0.39 | 0.28 | 1.42 | 0.33 | 0.10 |
| 25 | 0.85 | 0.48 | 0.32 | 1.67 | 2.34 | 1.44 |
| 26 | 1.01 | 0.54 | 0.74 | 2.16 | 3.92 | 2.43 |
| 27 | 1.35 | 0.89 | 0.63 | 2.65 | 4.53 | 2.62 |
| 28 | 0.56 | 0.26 | 0.07 | 1.15 | 2.19 | 1.44 |
| 29 | 0.27 | 0.20 | 0.23 | 0.44 | 0.68 | 0.36 |
| 30 | 0.32 | 0.13 | 0.00 | 0.62 | 0.64 | 0.22 |
| 31 | 90.67 | 94.07 | 93.82 | 84.78 | 81.73 | 88.72 |
| 32 | 0.25 | 0.15 | 0.00 | 0.12 | 0.00 | 0.00 |
| 33 | 0.14 | 0.08 | 0.00 | 0.33 | 0.11 | 0.00 |
| Total paraffins | 96.4 | 97.4 | 96.3 | 96.7 | 96.5 | 97.3 |
| Mononaphthenes (wt %) | | | | | | |
| 21 | 0.00 | 0.00 | 0.00 | 0.00 | 0.00 | 0.00 |
| 22 | 0.00 | 0.00 | 0.00 | 0.00 | 0.00 | 0.00 |
| 23 | 0.00 | 0.00 | 0.00 | 0.00 | 0.00 | 0.00 |
| 24 | 0.00 | 0.00 | 0.00 | 0.06 | 0.00 | 0.00 |
| 25 | 0.09 | 0.00 | 0.00 | 0.07 | 0.00 | 0.00 |
| 26 | 0.10 | 0.00 | 0.00 | 0.06 | 0.00 | 0.00 |
| 27 | 0.21 | 0.00 | 0.07 | 0.18 | 0.14 | 0.00 |
| 28 | 0.23 | 0.00 | 0.00 | 0.12 | 0.00 | 0.11 |
| 29 | 1.22 | 1.24 | 1.31 | 1.27 | 1.11 | 1.11 |
| 30 | 0.00 | 0.00 | 0.00 | 0.00 | 0.00 | 0.00 |
| 31 | 1.76 | 1.38 | 2.31 | 1.55 | 2.24 | 1.45 |
| 32 | 0.00 | 0.00 | 0.00 | 0.00 | 0.00 | 0.00 |
| 33 | 0.00 | 0.00 | 0.00 | 0.00 | 0.00 | 0.00 |
| Total mononapht. | 3.6 | 2.6 | 3.7 | 3.3 | 3.5 | 2.7 |

FIG. 2 shows the FIMS analysis of entry I of table 1, and FIGS. 3 and 4 shows the FIMS analysis of entries A-K.

Example 2—Properties of the $C_{31}$ Renewable Base Oil

FIG. 2 shows the FIMS analysis of entry I of table 1. A number of properties of the $C_{31}$ renewable base oil of entry I of table 1 were measured and compared to other commercial base oils, see table 2, where the Pour Point was measured using ASTM D5950; Viscosity using EN ISO 3104; paraffins and naphthenes using the FIMS method; Viscosity index using ASTM D2270; CCS viscosity using ASTM D5293; Noack number using CECL-40-93-B.

TABLE 2

Properties of the $C_{31}$ renewable base oil (RBO) and other commercially available base oils

| | | $C_{31}$ RBO | NB 3035 | NB 3043 | NB 3050 | GTL4 | PAO4 | Yubase4+ |
|---|---|---|---|---|---|---|---|---|
| API Group | | III | II | III | III | III+ | IV | III+ |
| Pour point | ° C. | −20 | −37 | −21 | −17 | −35 | −76 | −20 |
| Viscosity (100° C.) | mm²/s | 4.3 | 3.5 | 4.3 | 5.0 | 4.1 | 4.0 | 4.2 |
| Viscosity (40° C.) | mm²/s | 18.0 | 14.7 | 20.3 | 25.3 | 18.2 | 17.8 | 18.3 |
| Viscosity Index | | 155 | 114 | 121 | 130 | 129 | 123 | 133 |
| CCS −30° C. viscosity | mPas | 920 | 860 | 1660 | 2410 | 1090 | 850 | 1115 |
| CCS −35° C. viscosity | mPas | 1560 | 1490 | 3000 | 4540 | 1870 | 1390 | 1982 |

TABLE 2-continued

Properties of the $C_{31}$ renewable base oil (RBO) and other commercially available base oils

|  |  | $C_{31}$ RBO | NB 3035 | NB 3043 | NB 3050 | GTL4 | PAO4 | Yubase4+ |
|---|---|---|---|---|---|---|---|---|
| CCS −40° C. viscosity | mPas | 2910 | 2720 | 5920 | 9300 | 3330 | 2350 | 3450 |
| HTHS | mPas | 1.55 | 1.25 | 1.52 | 1.79 | 1.43 | 1.45 | 1.49 |
| Noack | wt-% | 8.3 | 23.8 | 14.1 | 8.6 | 12.1 | 12.6 | 12.9 |
| Paraffins | wt-% | 96.7 |  | 41.7 | 39.1 | 69.2 | 95.4 | 49.4 |
| Mono-naphthenes | wt-% | 3.3 |  | 35.8 | 38.1 | 27.9 | 4.6 | 26.1 |
| Di-naphthenes | wt-% | 0.0 |  | 18.2 | 18.0 | 2.7 | 0.0 | 10.9 |
| Tri-naphthenes | wt-% | 0.0 |  | 4.3 | 4.6 | 0.0 | 0.0 | 4.8 |
| Tetra-naphthenes | wt-% | 0.0 |  | 0.0 | 0.1 | 0.0 | 0.0 | 3.1 |
| Penta-naphthenes | wt-% | 0.0 |  | 0.0 | 0.0 | 0.2 | 0.0 | 2.6 |
| Hexa-naphthenes | wt-% | 0.0 |  | 0.0 | 0.0 | 0.0 | 0.0 | 3.1 |

NB 3035, 3043 and 3050 are NEXBASE ® 3035, 3043 and 3050 from Neste Oyj;
GTL4 is a Fischer-Tropsch derived oil;
PAO4 is a typical commercially available PAO, such as NEXBASE ® 2004 from Neste Oyj;
Yubase4+ is from SK.

Example 3—Comparison of 0W-30 Formulations of Different Base Oils with Formulations Containing $C_{31}$ Renewable Base Oil A simulation model was created for a number of base oils, a commercial passenger car motor oil (PCMO) additive package and a commercial viscosity index improver (VII). The simulation model was used to prepare cost optimised 0W-30 formulations of the different base oils (assuming the costs of the oils being: PAO4, PAO6>$C_{31}$ RBO>GTL4, GTL8, Yb4+>GpIII>GpII). The results are shown in table 3, where the different amounts of base oils, additive package and VII are given to obtain as close to identical estimated properties (KV100, CCS-35° C., HTHS and Noack).

TABLE 3

Model results of cost optimized 0W-30 formulations with different base oils

|  |  | Yb4+ based | PAO based | GTL based | RBO based |
|---|---|---|---|---|---|
| Additive package |  | 15.3 | 15.3 | 15.3 | 15.3 |
| Viscosity Index Improver | VII | 19.90 | 20.57 | 21.26 | 20.70 |
| NEXBASE ® 3035 | GpII |  |  |  | 12.95 |
| NEXBASE ® 3043 | GpIII |  | 0.86 |  |  |
| NEXBASE ® 3050 | GpIII |  | 15.81 |  | 12.00 |
| PAO4 | GpIV | 22.00 | 47.46 | 5.82 |  |
| PAO6 | GpIV | 13.0 |  | 7.05 |  |
| $C_{31}$ RBO | RBO |  |  |  | 39.05 |
| Yubase4+ | GpIII+ | 29.80 |  |  |  |
| GTL4 | GpIII+ |  |  | 50.57 |  |
| GTL8 | GpIII+ |  |  |  |  |
| Total |  | 100 | 100 | 100 | 100 |
| Estimated results |  |  |  |  |  |
| Viscosity (100° C.) | mm²/s | 11.92 | 11.98 | 12.12 | 12.07 |
| CCS −35° C. viscosity | mPas | 5897 | 5897 | 5897 | 5897 |
| HTHS | mPas | 3.56 | 3.56 | 3.56 | 3.56 |
| Noack | wt-% | 10.45 | 10.45 | 10.45 | 10.45 |

NEXBASE ® 3035, 3043 and 3050 are from Neste Oyj; GTL4 and GTL 8 are Fischer-Tropsch derived oils; PAO4 and PAO6 is a typical commercially available PAO, such as NEXBASE ® 2004 and 2006 from Neste Oyj; Yubase4+ is from SK.

Example 4—a 0W-30 Test Blend Containing $C_{31}$ Renewable Base Oil

A test blend comprising the PCMO additive package, VII, NEXBASE® 3043 and the $C_{31}$ RBO was prepared and its properties measured. The test blend fulfilled the requirements for a SAE grade 0W-30 oil.

TABLE 4

Test blend of a 0W-30 formulation with the $C_{31}$ renewable base oil ($C_{31}$ RBO)

|  |  | $C_{31}$ RBO based |
|---|---|---|
| Additive package |  | 12.6 |
| Viscosity Index Improver | VII | 20.0 |
| NEXBASE ® 3035 | GpII | 0.0 |
| NEXBASE ® 3043 | GpIII | 6.8 |
| NEXBASE ® 3050 | GpIII | 0.0 |
| PAO4 | GpIV | 0.0 |
| PAO6 | GpIV | 0.0 |
| $C_{31}$ RBO | RBO | 60.6 |
| Yubase4+ | GpIII+ | 0.0 |
| GTL4 | GpIII+ | 0.0 |
| GTL8 | GpIII+ | 0.0 |
| Total |  | 100 |
| Test results |  |  |
| Viscosity (100° C.) | mm²/s | 11.03 |
| Viscosity (40° C.) | mm²/s | 51.02 |
| CCS −30° C. viscosity | mPas | 2540 |
| CCS −35° C. viscosity | mPas | 4520 |
| CCS −40° C. viscosity | mPas | 8780 |
| HTHS | mPas | 3.34 |
| Noack | wt-% | 9.0 |
| Pour point | ° C. | −33 |

Example 5—SAE Grade 0W-XX Test Blends Containing $C_{31}$ Renewable Base Oil

A number of test blends comprising the PCMO additive package, without (blends 1-6) and with (blends 7-12) a viscosity index improver, were made from different base oils including the $C_{31}$ RBO. The properties and SAE grade were measured and provided in tables 5 and 6 below.

TABLE 5

Test blends 1-6 (B1-B6) of 0W-XX formulations with the $C_{31}$ renewable base oil (RBO) and without a viscosity index improver (VII).

|  |  | B1 | B2 | B3 | B4 | B5 | B6 |
|---|---|---|---|---|---|---|---|
| Additive package |  | 12.6 | 12.6 | 12.6 | 12.6 | 12.6 | 12.6 |
| Viscosity Index Improver | VII |  |  |  |  |  |  |
| NEXBASE ® 3035 | GpII |  |  |  | 30.0 |  |  |
| NEXBASE ® 3043 | GpIII |  |  |  |  |  |  |
| PAO4 | GpIV |  | 87.4 |  |  |  |  |
| $C_{31}$ RBO | RBO | 87.4 |  |  | 57.4 |  |  |
| Yubase4+ | GpIII+ |  |  | 87.4 |  |  |  |
| GTL4 | GpIII+ |  |  |  |  | 87.4 | 77.4 |
| GTL8 | GpIII+ |  |  |  |  |  | 10.0 |
| Total |  | 100 | 100 | 100 | 100 | 100 | 100 |
|  |  | Test results |  |  |  |  |  |
| SAE Grade (J300) |  | 0W-12 | 0W-8 | 0W-12 | 0W-8 | 0W-8 | 0W-12 |
| Viscosity (100° C.) | mm$^2$/s | 6.00 | 5.69 | 5.91 | 5.68 | 5.79 | 6.17 |
| Viscosity (40° C.) | mm$^2$/s | 27.78 | 28.11 | 28.87 | 26.49 | 28.69 | 31.41 |
| CCS −30° C. viscosity | mPas | 1730 | 1710 | 2290 | 1730 | 2130 | 2500 |
| CCS −35° C. viscosity | mPas | 3066 | 2830 | 4130 | 2997 | 3700 | 4370 |
| CCS −40° C. viscosity | mPas | 5963 | 4910 | 8040 | 5686 | 6720 | 8070 |
| HTHS | mPas | 2.08 | 1.93 | 2.07 | 1.98 | 1.99 | 2.11 |
| Noack | wt-% | 7.8 | 10.3 | 11.6 | 12.4 | 10.4 | 10 |
| Pour point | ° C. | −27 | −71 | −19 | −21 | −58 | −46 |

TABLE 6

Test blends 7-12 (B7-B12) of 0W-XX formulations with the $C_{31}$ renewable base oil (RBO) and with 10 wt % of a viscosity index improver (VII).

|  |  | B7 | B8 | B9 | B10 | B11 | B12 |
|---|---|---|---|---|---|---|---|
| Additive package |  | 12.6 | 12.6 | 12.6 | 12.6 | 12.6 | 12.6 |
| Viscosity Index Improver | VII | 10.0 | 10.0 | 10.0 | 10.0 | 10.0 | 10.0 |
| NEXBASE ® 3035 | GpII |  |  |  | 30.0 |  |  |
| NEXBASE ® 3043 | GpIII |  |  |  |  |  |  |
| PAO4 | GpIV |  | 77.4 |  |  |  |  |
| $C_{31}$ RBO | RBO | 77.4 |  |  | 47.4 |  |  |
| Yubase4+ | GpIII+ |  |  | 77.4 |  |  |  |
| GTL4 | GpIII+ |  |  |  |  | 77.4 | 67.4 |
| GTL8 | GpIII+ |  |  |  |  |  | 10.0 |
| Total |  | 100 | 100 | 100 | 100 | 100 | 100 |
|  |  | Test results |  |  |  |  |  |
| SAE Grade (J300) |  | 0W-20 | 0W-16 | 0W-20 | 0W-16 | 0W-16 | 0W-20 |
| Viscosity (100° C.) | mm$^2$/s | 7.95 | 7.63 | 8.10 | 7.74 | 7.74 | 8.19 |
| Viscosity (40° C.) | mm$^2$/s | 37.00 | 37.30 | 38.70 | 35.57 | 38.23 | 41.71 |
| CCS −30° C. viscosity | mPas | 2030 | 1930 | 2630 | 2033 | 2450 | 2880 |
| CCS −35° C. viscosity | mPas | 3570 | 3227 | 4790 | 3573 | 4270 | 5060 |
| CCS −40° C. viscosity | mPas | 6983 | 5683 | 9500 | 6830 | 7890 | 9400 |
| HTHS | mPas | 2.65 | 2.47 | 2.66 | 2.58 | 2.53 | 2.69 |
| Noack | wt-% | 8.1 | 9.8 | 11.3 | 12.8 | 11 | 9.7 |
| Pour point | ° C. | −30 | −61 | −31 | −31 | −44 | −32 |

The HTHS and KV100 are two of the important properties of low viscosity SAE grade oils. These two properties have been plotted in FIG. 6 to show that it is possible to obtain the different SAE J300 grades using the $C_{31}$ RBO.

The SAE 20, 16, 12 and 8 minimum HTHS are 2.6, 2.3, 2.0 and 1.7 mPas, respectively (SAE J300_201501). J300 specifies that the 100° C. kinematic viscosities (KV100) for the same SAE 20, SAE 16, SAE 12, SAE 8 overlap to provide adequate formulating space for these grades. FIG. 6 shows that the $C_{31}$ RBO may be blended to fit all SAE grades from SAE 0W-20 to SAE 0W-8.

The invention claimed is:

1. A lubricating oil composition comprising:
    a) a base oil mixture containing:
    at least 13 wt % of a renewable base oil;
    a remainder selected from one or more base oils in a same or different API (American Petroleum Institute) category;
    wherein the amounts of renewable base oil given in wt % are based on a total base oil mixture; and
    b) one or more performance additives;
    wherein the renewable base oil contains:
    i) more than 80 wt % $C_{31}$ alkanes;
    ii) less than 10 wt % $C_{32}$ or higher alkanes; and
    iii) less than 9 wt % cycloalkanes;
    being given in wt % based on the renewable base oil; and
    wherein the at least one or more performance additives are selected from a list consisting of: antioxidants, metal deactivators, corrosion inhibitors, detergents, dispersants, antiwear additives, friction modifiers, pour point depressants, viscosity improvers, foam inhibitors, thickeners, demulsifiers, emulsifiers, bactericides, fungicides and tackiness additives;
    weight percentages of hydrocarbon composition of the renewable base oil being measured using field ionisation mass spectrometry (FI-MS).

2. The lubricating oil composition according to claim 1, being configured for meeting specifications for 0W-XX, including any one of 0W-20, 0W-16, 0W-12, or 0W-8.

3. The lubricating oil composition according to claim 1, wherein the renewable base oil comprises at least one of:
    the alkanes including 70 wt % or more iso-alkanes; and
    less than 1 wt % of oxygen-containing compounds;
    weight percentages of hydrocarbons being measured using field ionisation mass spectrometry (FI-MS).

4. The lubricating oil composition according to claim 1, wherein the renewable base oil comprises:
    between 1 wt % and 20 wt % $C_{20-30}$ alkanes;
    between 0.1 wt % and 10 wt % $C_{32}$ or higher alkanes;
    between 1 wt % and 8 wt % $C_{25-32}$ cycloalkanes;
    less than 1 wt % aromatic hydrocarbons; and
    less than 2 wt % di-, tri-, tetra- naphthenes, or higher;
    weight percentages of the hydrocarbons being measured using field ionisation mass spectrometry (FI-MS).

5. The lubricating oil composition according to claim 1, wherein in the renewable base oil at least one of the following conditions is satisfied:
    a combined amount of $C_{29}$ and $C_{30}$ alkanes in wt % is less than a combined amount of $C_{26}$ and $C_{27}$ alkanes in wt %; and
    a combined amount of $C_{29}$ and $C_{31}$ cycloalkanes in wt % is more than a combined amounts of $C_{25}$, $C_{26}$, $C_{27}$, $C_{28}$, $C_{30}$ cycloalkanes; and
    weight percentages of hydrocarbons is measured using field ionisation mass spectrometry (FI-MS).

6. The lubricating oil composition according to claim 1, wherein the renewable base oil has at least one or more of the following properties:
    a boiling point of between 350° C. and 650° C. as measured ASTM D7500;
    a viscosity index (VI) of more than 140 as measured using ASTM D2270;
    a Noack volatility number of less than 10 wt % as measured using ASTM D5800 or CECL-40-93-B;
    a pour point of –6° C. or lower as measured using ASTM D7346;
    a Cold-Cranking Simulator viscosity (CCS–35° C.) value of less than 1800 cP as measured using ASTM D5293; and
    a kinematic viscosity (kV100) of less than 5 cSt using EN ISO 3104.

7. The lubricating oil composition according to claim 1, wherein:
    the renewable base oil has a kinematic viscosity at 100° C. (kV100) of 16 cSt as measured using ASTM D445; and
    the composition has a Noack volatility of at most 11% as measured using CECL-40-93-B.

8. The lubricating oil composition according to claim 1, wherein the renewable base oil is present in an amount of at least 35 wt % based on the total base oil mixture.

9. The lubricating oil composition according to claim 1, wherein the base oil mixture in addition to the at least 13 wt % of a renewable base oil, comprises:
    two or more base oils in a same or different API category.

10. The lubricating oil composition according to claim 1, wherein at least one of following conditions is satisfied:
    the oil lubricating composition contains 10-50 wt %, based on the total base oil mixture, of a Group II and/or Group III base oil;
    the base oil mixture contains no more than 10 wt % of a polyalphaolefin base oil; and
    the base oil mixture contains no more than 10 wt % of a Fischer-Tropsch derived base oil.

11. The lubricating oil composition according to claim 1, wherein the content of the renewable base oil is between 15 and 95 wt %, based on the total base oil mixture.

12. The lubricating oil composition according to claim 1, wherein the renewable base oil has less than 4.5 wt % cycloalkanes.

13. A base oil composition comprising:
    between 80 wt % and 95 wt % $C_{31}$ alkanes;
    less than 10 wt % $C_{32}$ or higher alkanes;
    the alkanes and high alkanes including 70 wt % or more iso-alkanes;
    less than 9 wt %, cycloalkanes; and
    weight percentages of hydrocarbons are measured using field ionisation mass spectrometry (FI-MS).

14. The base oil composition according to claim 13, comprising:
    between 1 wt % and 10 wt % $C_{20-30}$ alkanes;
    weight percentages of hydrocarbons being measured using field ionisation mass spectrometry (FI-MS).

15. The base oil composition according to claim 13, wherein at least one of the following conditions is satisfied:
    a combined amount of $C_{29}$ and $C_{30}$ alkanes in wt % is less than a combined amount of $C_{26}$ and $C_{27}$ alkanes in wt %; and
    a combined amount of $C_{29}$ and $C_{31}$ cycloalkanes in wt % is more than combined amounts of $C_{25}$, $C_{26}$, $C_{27}$, $C_{28}$, $C_{30}$ cycloalkanes;

weight percentages of the hydrocarbons are measured using field ionisation mass spectrometry (FI-MS).

16. The base oil composition according to claim 13, wherein the composition comprises:
   less than 0.5 wt % aromatic hydrocarbons;
   less than 0.5 wt % di-, tri-, tetra- naphthenes, or higher;
   less than 1 wt % of oxygen-containing compounds;
   less than 300 ppm sulfur content as measured using ASTM D 3120; and
   less than 100 ppm nitrogen content as measured using ASTM D 4629;
      weight percentages of hydrocarbons are measured using field ionisation mass spectrometry (FI-MS).

17. The base oil composition according to claim 13 having one or more of the following properties:
   a boiling point of between 350° C. and 650° C. as measured using ASTM D7500;
   a viscosity index (VI) of more than 140 as measured using ASTM D2270;
   a Noack volatility number of less than 10 wt % as measured using ASTM D5800 or CECL-40-93-B;
   a pour point of less than −10° C. as measured using ASTM D7346;
   a Cold-Cranking Simulator viscosity (CCS−35° C.) of less than 1800 cP as measured using ASTM D5293;
   a Cold-Cranking Simulator viscosity (CCS−30° C.) of less than 1300 mPas as measured using ASTM D5293; and
   a kinematic viscosity at 100° C. (KV100) of less than 5 mm$^2$/s using EN ISO 3104.

18. The base oil composition of claim 13 having at least the following properties:
   a Noack volatility number of less than 10 wt % as measured using ASTM D5800 or CECL-40-93-B; and
   a kinematic viscosity at 100° C. (KV100) of less than 5 mm$^2$/s using EN ISO 3104.

19. The base oil composition of claim 13, where a pour point of the $C_{31}$ base oil is less than −5° C. as measured using ASTM D7346.

20. The base oil composition of claim 13, comprising:
   at least 95 wt % hydrocarbons.

21. The base oil composition of claim 13, comprising:
   at least 90 wt % alkanes.

22. The base oil composition of claim 13, where the iso-alkanes comprise:
   at least three different structural isomers of the $C_{31}$ alkanes.

23. A base oil mixture comprising,
   at least 11 wt % of a base oil composition according to claim 13; and
   a remainder selected from one or more base oils in a same or in different API (American Petroleum Institute) category;
   wherein amounts given in wt % are based on a total base oil mixture;
   wherein the composition has a kinematic viscosity at 100° C. (KV100) of 16 cSt as measured using ASTM D445; and
   wherein the composition has a Noack volatility of at most 11% as measured using CECL-40-93-B.

24. The base oil mixture according to claim 23, wherein the base oil composition is present in an amount of at least 35 wt % based on a total base oil.

25. The base oil mixture according to claim 23, wherein the base oil mixture in addition to the at least 11 wt % of a base oil composition, comprises: two or more base oils in a same or different API category.

26. The base oil mixture according to claim 23, where the base oil mixture contains at least one of:
   10-50 wt % based on a total base oil mixture of a Group II and/or Group III base oil;
   no more than 10 wt % of an polyalphaolefin base oil; and
   no more than 10 wt % of a Fischer-Tropsch derived base oil.

27. The base oil mixture according to claim 23, wherein a content of the base oil composition is between 15 and 95 wt %.

28. A method for reducing the Noack volatility and/or kinematic viscosity at 100° C. (KV100) of a lubricating oil composition the method comprising:
   providing a lubricating oil composition; and
   forming a base oil mixture, including the renewable base oil and one or more performance additives;
   wherein the renewable base oil is a base oil composition as defined in claim 13 in an amount of at least 11 wt % based on a total base oil mixture;
   wherein the composition has a kinematic viscosity at 100° C. (KV100) of 9.3 mm$^2$/s or less as measured using ASTM D445; and
   wherein the composition has a Noack volatility of at most 11% as measured using CECL-40-93-B; and
   wherein the at least one or more performance additives are selected from a list consisting of: antioxidants, metal deactivators, corrosion inhibitors, detergents, dispersants, antiwear additives, friction modifiers, pour point depressants, viscosity improvers, foam inhibitors, thickeners, demulsifiers, emulsifiers, bactericides, fungicides and tackiness additives.

29. The lubricating oil composition according to claim 1, wherein
   the renewable base oil content is between 20 and 90 wt %, based on total base oil mixture.

30. The base oil composition according to claim 13, containing less than 4.5 wt % cycloalkanes.

31. The base oil mixture according to claim 23, wherein the base oil composition is present in an amount of at least 50 wt % based on a total base oil mixture.

* * * * *